(12) United States Patent
Yamada

(10) Patent No.: US 11,707,186 B2
(45) Date of Patent: Jul. 25, 2023

(54) FLUORESCENCE OR AUTO-FLUORESCENCE TRIGGER OR TRIGGERS

(71) Applicant: Canon U.S.A., Inc., Melville, NY (US)

(72) Inventor: Daisuke Yamada, Cambridge, MA (US)

(73) Assignee: Canon U.S.A., Inc., Melville, NY (US)

(*) Notice: Subject to any disclaimer, the term of this patent is extended or adjusted under 35 U.S.C. 154(b) by 465 days.

(21) Appl. No.: 16/898,293

(22) Filed: Jun. 10, 2020

(65) Prior Publication Data
US 2020/0390323 A1    Dec. 17, 2020

Related U.S. Application Data

(60) Provisional application No. 62/861,888, filed on Jun. 14, 2019.

(51) Int. Cl.
*A61B 1/04* (2006.01)
*A61B 1/015* (2006.01)
(Continued)

(52) U.S. Cl.
CPC ............ *A61B 1/043* (2013.01); *A61B 1/0002* (2013.01); *A61B 1/00009* (2013.01);
(Continued)

(58) Field of Classification Search
CPC ............ A61B 1/00006; A61B 1/00009; A61B 1/0002; A61B 1/00036; A61B 1/00126;
(Continued)

(56) References Cited

U.S. PATENT DOCUMENTS

| 5,303,026 A | 4/1994 | Strobl et al. |
| 6,069,689 A | 5/2000 | Zeng et al. |

(Continued)

FOREIGN PATENT DOCUMENTS

| JP | 2010-158343 A | 7/2010 |
| WO | 2015/116939 A1 | 8/2015 |

(Continued)

OTHER PUBLICATIONS

Yoo, H., et al., "Intra-arterial catheter for simultaneous microstructural and molecular imaging in vivo", Nat Med, vol. 17, No. 12, Jun. 2012, pp. 1680-1684.

(Continued)

*Primary Examiner* — Mark D Remaly
(74) *Attorney, Agent, or Firm* — Canon U.S.A., Inc. I.P. Division

(57) ABSTRACT

One or more triggers, fluorescence or auto-fluorescence triggers, NIRAF triggers, methods of using triggers, fiber optic rotary joints (FORJ), free space beam combiners, OCT, SEE and/or fluorescence devices and systems for use therewith, methods of using and/or manufacturing same and storage mediums are provided. One or more embodiments using one or more triggers achieve structural compactness and/or high-speed acquisition while avoiding or reducing the need for high computational power. One or more embodiments use one or more triggers, one or more fluorescence triggers, one or more auto-fluorescence triggers, or NIRAF triggers, and/or one or more rotary joints, for performing pullback and/or image recording. Examples of optical applications that may involve the use of a trigger, fluorescence/auto-fluorescence trigger or NIRAF trigger, and/or a fiber optic rotary joint, include imaging, evaluating and characterizing/identifying biological objects or tissue, such as, but (Continued)

not limited to, for gastro-intestinal, otolaryngologic, cardio and/or ophthalmic applications.

14 Claims, 13 Drawing Sheets

(51) Int. Cl.
| | |
|---|---|
| A61B 1/313 | (2006.01) |
| A61B 1/045 | (2006.01) |
| A61B 1/00 | (2006.01) |
| A61B 5/00 | (2006.01) |
| A61B 1/07 | (2006.01) |
| A61B 1/06 | (2006.01) |
| A61B 90/00 | (2016.01) |
| A61M 5/00 | (2006.01) |

(52) U.S. Cl.
CPC ...... *A61B 1/00036* (2013.01); *A61B 1/00126* (2013.01); *A61B 1/015* (2013.01); *A61B 1/045* (2013.01); *A61B 1/0638* (2013.01); *A61B 1/0646* (2013.01); *A61B 1/07* (2013.01); *A61B 1/3137* (2013.01); *A61B 5/0035* (2013.01); *A61B 5/0066* (2013.01); *A61B 5/0071* (2013.01); *A61B 2090/3735* (2016.02); *A61M 5/007* (2013.01)

(58) Field of Classification Search
CPC . A61B 1/00165; A61B 1/00172; A61B 1/015; A61B 1/043; A61B 1/045; A61B 1/0638; A61B 1/0646; A61B 1/0684; A61B 1/07; A61B 1/3137; A61B 2090/3735; A61B 5/0035; A61B 5/0066; A61B 5/0071; A61M 5/007
See application file for complete search history.

(56) References Cited

U.S. PATENT DOCUMENTS

| | | | |
|---|---|---|---|
| 6,341,036 B1 | 1/2002 | Tearney et al. | |
| 6,763,261 B2 | 7/2004 | Casscells, III et al. | |
| 7,428,048 B1 | 9/2008 | Farkas et al. | |
| 7,447,408 B2 | 11/2008 | Bouma et al. | |
| 7,508,524 B2 | 3/2009 | Mahadevan-Jansen et al. | |
| 7,551,293 B2 | 6/2009 | Yelin et al. | |
| 7,749,168 B2 | 7/2010 | Maschke et al. | |
| 7,796,270 B2 | 9/2010 | Yelin et al. | |
| 7,859,679 B2 | 12/2010 | Bouma et al. | |
| 7,872,759 B2 | 1/2011 | Tearney et al. | |
| 7,889,348 B2 | 2/2011 | Tearney et al. | |
| 7,952,706 B2 | 5/2011 | Ling et al. | |
| 7,952,719 B2 | 5/2011 | Brennan, III | |
| 8,035,819 B2 | 10/2011 | Zuluaga | |
| 8,045,177 B2 | 10/2011 | Tearney et al. | |
| 8,084,755 B2 | 12/2011 | Hall et al. | |
| 8,145,018 B2 | 3/2012 | Shishkov et al. | |
| 8,219,183 B2 | 7/2012 | Maschke et al. | |
| 8,289,522 B2 | 10/2012 | Tearney et al. | |
| 8,412,312 B2 | 4/2013 | Judell et al. | |
| 8,553,219 B2 | 10/2013 | Patil et al. | |
| 8,838,213 B2 | 9/2014 | Tearney et al. | |
| 8,928,889 B2 | 1/2015 | Tearney et al. | |
| 9,179,845 B2 | 11/2015 | Farcy et al. | |
| 9,254,089 B2 | 2/2016 | Tearney et al. | |
| 9,286,673 B2 | 3/2016 | Begin et al. | |
| 9,295,391 B1 | 3/2016 | Tearney et al. | |
| 9,301,687 B2 | 4/2016 | Kemp | |
| 9,332,942 B2 | 5/2016 | Jaffer et al. | |
| 9,415,550 B2 | 8/2016 | Tearney et al. | |
| 9,526,424 B2 | 12/2016 | Judell et al. | |
| 9,557,154 B2 | 1/2017 | Tearney et al. | |
| 9,795,301 B2 | 10/2017 | Fleming et al. |
| 9,869,828 B2 | 1/2018 | Altshuler |
| 10,130,259 B2 | 11/2018 | Lam et al. |
| 2008/0228086 A1 | 9/2008 | Ilegbusi et al. |
| 2009/0192358 A1 | 7/2009 | Jaffer et al. |
| 2010/0092389 A1 | 4/2010 | Jaffer |
| 2010/0315632 A1 | 12/2010 | Brennan, III |
| 2011/0071405 A1 | 3/2011 | Judell et al. |
| 2011/0292400 A1 | 12/2011 | Fleming et al. |
| 2011/0299091 A1 | 12/2011 | Yun et al. |
| 2012/0101374 A1 | 4/2012 | Tearney et al. |
| 2014/0276011 A1 | 9/2014 | Schmitt et al. |
| 2015/0080686 A1 | 3/2015 | Karlheinz et al. |
| 2016/0228097 A1 | 8/2016 | Jaffer et al. |
| 2016/0335766 A1 | 11/2016 | Ambwani et al. |
| 2017/0035281 A1 | 2/2017 | Takeuchi et al. |
| 2017/0135584 A1 | 5/2017 | Tearney et al. |
| 2017/0196459 A1 | 7/2017 | Lam et al. |
| 2017/0209049 A1 | 7/2017 | Wang et al. |
| 2018/0017778 A1 | 1/2018 | Ikuta et al. |
| 2018/0055953 A1 | 3/2018 | Jaffer et al. |
| 2018/0136129 A1 | 5/2018 | Rizo et al. |
| 2018/0348439 A1 | 12/2018 | Yamada |
| 2019/0059734 A1 | 2/2019 | Yamada |
| 2019/0099079 A1 | 4/2019 | Yamada et al. |
| 2019/0298174 A1 | 10/2019 | Watanabe |
| 2019/0391338 A1 | 12/2019 | Tearney et al. |
| 2020/0085285 A1 | 3/2020 | Yamada |
| 2020/0256661 A1 | 8/2020 | Yamada |

FOREIGN PATENT DOCUMENTS

| | | |
|---|---|---|
| WO | 2015/116951 A2 | 8/2015 |
| WO | 2017/024145 A1 | 2/2017 |

OTHER PUBLICATIONS

Dixon, A.J., et al., "Intravascular near-infrared fluorescence catheter with ultrasound guidance and blood attenuation correction", J. Biomed Opt., vol. 18, No. 5, May 2013, pp. 056009-1 to 056009-9 (and title page).

Hao Wang, "Near infrared autofluorescence augmentation of optical coherence tomography for diagnosis of coronary atherosclerosis", Thesis/Dissertation, Boston University College of Engineering, Jan. 2014, (251 pages).

Dinglong Ma, et al., "Rotational multispectral fluorescence lifetime imaging and intravascular ultrasound: bimodal system for intravascular applications", Journal of Biomedical Optics, vol. 19, Issue 6, Jun. 2014, title page and pp. 066004-1 through 066004-11, available at https://www.spiedigitallibrary.org/journals/journal-of-biomedical-optics/volume-19/issue-06/066004/Rotational-multispectral-fluorescence-lifetime-imaging-and-intravascular-ultrasound--bimodal/10.1117/1.JBO.19.6.066004.full?SSO=1.

Giovanni J. Ughi, et al., "Dual modality intravascular optical coherence tomography (OCT) and near-infrared fluorescence (NIRF) imaging: a fully automated algorithm for the distance-calibration of NIRF signal intensity for quantitative molecular imaging", Int J Cardiovasc Imaging, vol. 31, No. 2, Feb. 2015, pp. 259-268 (18 pages total in attachment).

Hao Wang, et al., "Ex vivo catheter-based imaging of coronary atherosclerosis using multimodality OCT and NIRAF excited at 633 nm", Biomedical Optical Express, vol. 6, No. 4, Apr. 1, 2015, pp. 1363-1375.

Loretta Scolaro, et al., "Molecular imaging needles: dual-modality optical coherence tomography and fluorescence imaging of labeled antibodies deep in tissue", Biomedical Optics Express, Optical Society of America, vol. 6, No. 5, May 2015, pp. 1767-1781, available at https://www.ncbi.nlm.nih.gov/pmc/articles/PMC4467702/.

Shengnan Liu, et al., "Analysis and compensation for the effect of the catheter position on image intensities in intravascular optical coherence tomography", Journal of Biomedical Optics, vol. 21, No. 12, Dec. 2016, pp. 126005-1 to 126005-9 (and title page).

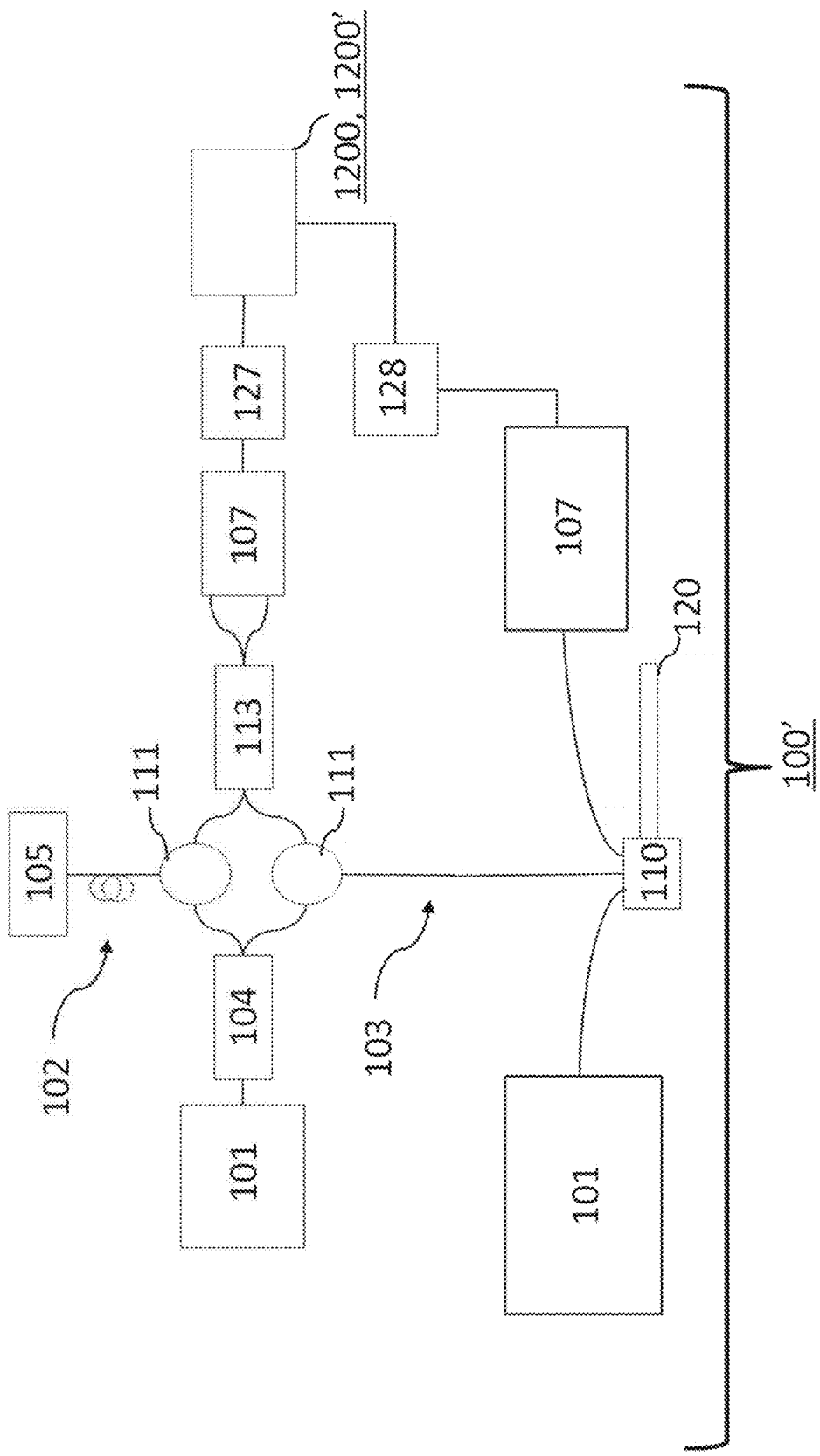

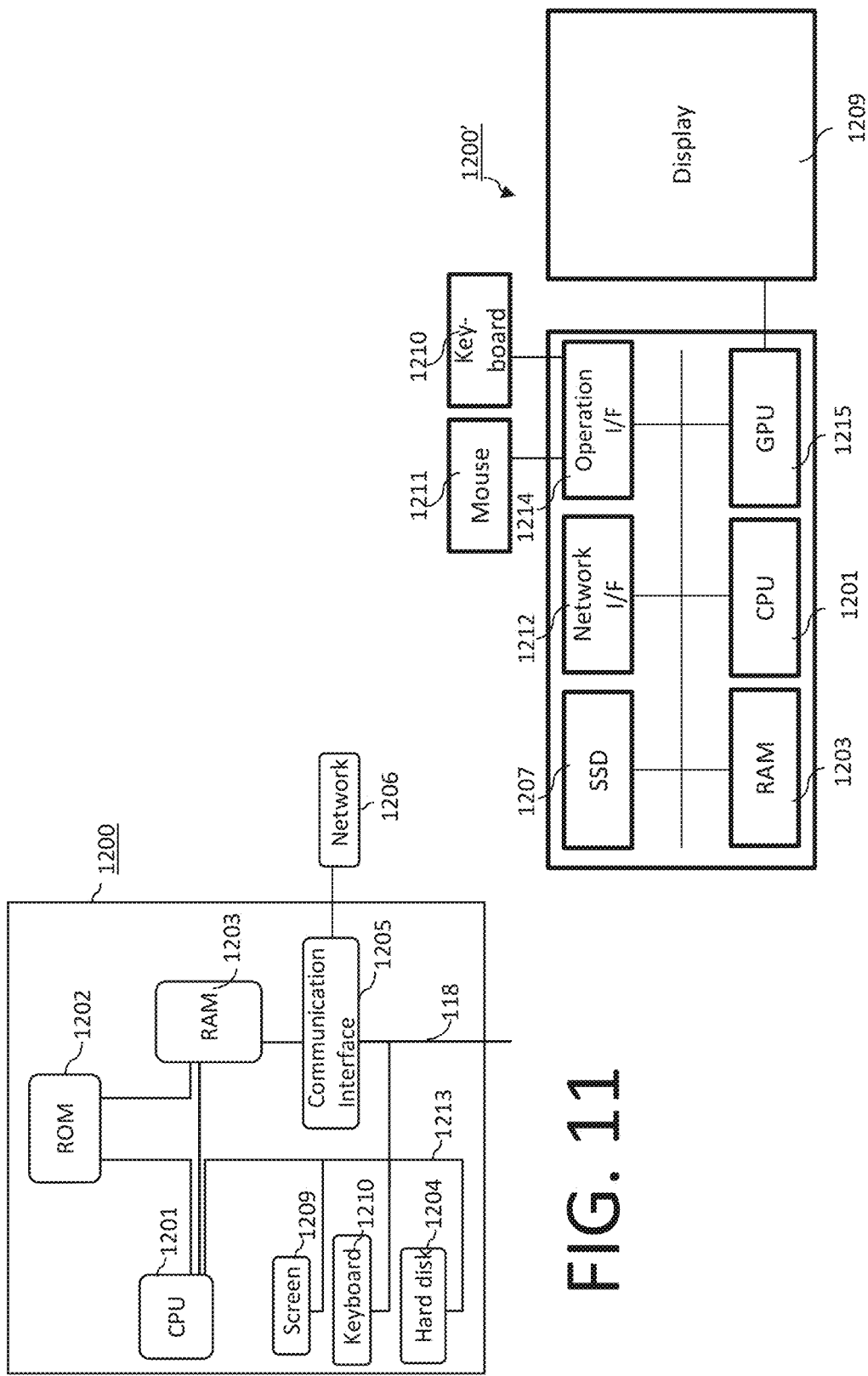

FLUORESCENCE OR AUTO-FLUORESCENCE TRIGGER OR TRIGGERS

CROSS-REFERENCE TO RELATED APPLICATION(S)

This application relates, and claims priority, to U.S. Patent Application Ser. No. 62/861,888, filed Jun. 14, 2019, the entire disclosure of which is incorporated by reference herein in its entirety.

FIELD OF THE INVENTION

The present disclosure relates generally to the field of optical imaging and more particularly to one or more fluorescence method(s) or system(s) that may be used with one or more optical apparatuses, systems, methods (for using and/or manufacturing) and storage mediums, such as, but not limited to, fiber optic catheters, endoscopes and/or optical coherence tomography (OCT) and/or fluorescence apparatuses and systems, spectroscopy apparatuses and systems, and methods and storage mediums for use with same, to achieve structural compactness and/or high speed acquisition while avoiding or reducing the need for high computational power, including, but not limited to, using one or more triggers for performing pullback and/or image recording. Examples of optical applications that may involve the use of a fiber optic rotary joint include imaging, evaluating and characterizing/identifying biological objects or tissue, such as, but not limited to, for gastro-intestinal, otolaryngologic, cardio and/or ophthalmic applications.

BACKGROUND OF THE INVENTION

Fiber optic catheters and endoscopes have been developed to access to internal organs. For example in cardiology, OCT (optical coherence tomography) has been developed to see depth resolved images of vessels with a catheter. The catheter, which may include a sheath, a coil and an optical probe, may be navigated to a coronary artery.

Optical coherence tomography (OCT) is a technique for obtaining high-resolution cross-sectional images of tissues or materials, and enables real time visualization. The aim of the OCT techniques is to measure the time delay of light by using an interference optical system or interferometry, such as via Fourier Transform or Michelson interferometers. A light from a light source delivers and splits into a reference arm and a sample (or measurement) arm with a splitter (e.g., a beamsplitter). A reference beam is reflected from a reference mirror (partially reflecting or other reflecting element) in the reference arm while a sample beam is reflected or scattered from a sample in the sample arm. Both beams combine (or are recombined) at the splitter and generate interference patterns. The output of the interferometer is detected with one or more detectors, such as, but not limited to, photodiodes or multi-array cameras, in one or more devices, such as, but not limited to, a spectrometer (e.g., a Fourier Transform infrared spectrometer). The interference patterns are generated when the path length of the sample arm matches that of the reference arm to within the coherence length of the light source. By evaluating the output beam, a spectrum of an input radiation may be derived as a function of frequency. The frequency of the interference patterns corresponds to the distance between the sample arm and the reference arm. The higher frequencies are, the more the path length differences are. Single mode fibers are commonly used for OCT optical probes, and double clad fibers are also commonly used for fluorescence and/or spectroscopy.

Spectrally encoded endoscope (SEE) is an endoscope technology that uses a broadband light source, a rotating or oscillating grating and a spectroscopic detector to encode spatial information from a sample. When illuminating light to the sample, the light is spectrally dispersed along one illumination line, such that the dispersed light illuminates a specific position of the illumination line with a specific wavelength. When the reflected light from the sample is detected with a spectrometer, the intensity distribution is analyzed as the reflectance along the line where the wavelength encodes the spatial information. By rotating or oscillating the grating to scan the illumination line, a two-dimensional image of the sample is obtained.

In order to acquire cross-sectional images of tubes and cavities such as vessels, and/or esophagus and nasal cavities, the optical probe is rotated with a fiber optic rotary joint (FORJ). A FORJ is the interface unit that operates to rotate one end of a fiber and/or an optical probe. In general, a free space beam coupler is assembled to separate a stationary fiber and a rotor fiber inside the FORJ. Besides, the optical probe may be simultaneously translated longitudinally during the rotation so that helical scanning pattern images are obtained. This translation is most commonly performed by pulling the tip of the probe back along a guidewire towards a proximal end and, therefore, referred to as a pullback.

A multi-modality system such as an OCT, fluorescence, and/or spectroscopy system with an optical probe is developed to obtain multiple information at the same time. The multi-modality FORJ has a beam combiner for at least two beams with multiple wavelengths to couple into the probe. Generally, lenses are assembled to make collimated beams for both stationary and rotor fibers in the beam combiner. Further, the detected light may be collected in the same or in one or more additional fibers, and, if rotating, these additional fibers may structurally interfere with each other.

It is difficult to make collimated beams for the common rotor fibers with different wavelengths, especially when the wavelength differences are large (e.g., in the range of 630 nm to 1300 nm, about double, etc.). An achromatic lens could be used to correct chromatic aberration; however, it is still difficult to control beam waist positions with multiple wavelengths to have high coupling efficiencies. Also, lenses with corrected aberrations are undesirably large, so a FORJ would become undesirably large (e.g., focal length and lens material(s) may increase size as well).

Imaging of coronary arteries by intravascular OCT systems may be developed to see blood vessel sizes and plaques from inside of vessels. However, blood cells strongly scatter the OCT light so that blood clearance is necessary to see lumen. Contrast agents, saline, dextran or other liquids are flushed to clear the blood cells. When blood cells are cleared, systems record OCT images with a pullback. A computer-implemented method may generate a trigger with computed OCT images to start automatically recording with the pullback. However, such a computer-implemented method requires computational power, and it is difficult to achieve high-speed real-time acquisition without a delay.

Accordingly, it would be desirable to provide at least one trigger or method for use in, or a way(s) to generate a trigger to control, at least one optical device, assembly or system to address one or more of the aforementioned inefficient and wasteful drawbacks, especially in a way that reduces or minimizes cost of manufacture, maintenance and/or use and/or in a way that achieves high speed acquisition with no use of high computational power and/or achieves a compact FORJ with high coupling efficiency.

SUMMARY OF THE INVENTION

Accordingly, it is a broad object of the present disclosure to provide triggers or methods, such as, but not limited to one or more fluorescence triggers, auto-fluorescence triggers, near-infrared autofluorescence (NIRAF) triggers, etc., that may be used with one or more optical apparatuses, systems, methods (for using and/or manufacturing) and storage mediums, such as, but not limited to, fiber optic catheters, endoscopes and/or optical coherence tomography (OC) apparatuses and systems, and methods and storage mediums, for use with same, to achieve high speed acquisition with no use of high computational power and/or to achieve structural compactness and high coupling efficiency.

Certain applications of OCT, such as multimodality OCT (MMOCT) systems/apparatuses, may use a fluorescence trigger, an auto-fluorescence trigger, a NIRAF trigger, etc. or method to control one or more devices, systems, etc.

In accordance with one or more embodiments of the present disclosure, apparatuses and systems, and methods and storage mediums for use with one or more embodiments of a fluorescence trigger, an auto-fluorescence trigger, a NIRAF trigger, etc. or method to control one or more devices, systems, etc. may operate to characterize biological objects, such as, but not limited to, blood, mucus, tissue, etc.

One or more embodiments of the present disclosure may performing imaging using an OCT system or sub-system that employs at least one fluorescence trigger, auto-fluorescence trigger, NIRAF trigger, etc. or method to control one or more devices, systems, etc. as discussed herein. Especially, the one or more apparatuses, systems, etc. are able to detect blood clearance and start measurements automatically based on fluorescence or auto-fluorescence light by blood cells. The one or more methods of the present disclosure do not require computing power, or high computing power, so that the one or more methods may achieve high-speed acquisition in real-time. For example, one or more embodiments may image coronary arteries by intravascular OC, and one or more embodiments may include an OCT and fluorescence multi-modality apparatus or system, and/or methods and storage mediums for use therewith. Such embodiments may employ or use a patient interface unit (PIU), and one or more embodiments of a PIU may include one or more of the following: a free space beam combiner, a FORJ, a rotational motor and translation motorized stage, and a catheter connector.

In accordance with one or more aspects of the present disclosure, at least one embodiment of a fluorescence trigger, an auto-fluorescence trigger, a NIRAF trigger, etc. or method to control one or more devices, systems, etc. for use in an apparatus or system may relate to forward and side views or imaging. Additionally or alternatively, one or more embodiments of a fluorescence trigger, an auto-fluorescence trigger, a NIRAF trigger, etc. or method to control one or more devices, systems, etc. for use in an apparatus or system may relate to using a photo diode. At least one embodiment may obtain one or more types of images (e.g., SEE, OCT, etc.).

One or more embodiments of the present disclosure may be used in clinical application(s), such as, but not limited to, intervascular imaging, atherosclerotic plaque assessment, cardiac stent evaluation, balloon sinuplasty, sinus stenting, arthroscopy, ophthalmology, ear research, veterinary use and research, etc.

One or more embodiments of the present disclosure may use at least one catheter, and one or more embodiments of the at least one catheter may include a sheath, a coil, a protector and an optical probe. The catheter may operate to be connected to one or more embodiments of the aforementioned PIU.

One or more embodiments of the present disclosure promote the use of blood clearance. When the blood is surrounded around the catheter, low fluorescence or auto-fluorescence from the blood cells may be detected. Then, when the blood cells are cleared by flushing media, such as, but not limited to, contrast agents, saline, and/or dextran, the fluorescence or auto-fluorescence signal intensities change because the flushing media is relatively transparent and has less fluorescence or auto-fluorescence. The excitation light may go through the flushing media but the blood cells due to the scattering properties, so when there are higher fluorescence or auto-fluorescence samples outside of the blood cells, the fluorescence or auto-fluorescence signal intensities may be elevated. Also, if there are no fluorescence or auto-fluorescence samples outside of the blood cells, the fluorescence or auto-fluorescence signal intensities may drop.

One or more additional embodiments of the present disclosure operate to generate a trigger, or use a method, by using fluorescence intensities, where fluorescence intensities are due to either intrinsic cellular fluorescence (auto-fluorescence) or fluorescence from an exogenous dye or marker.

One or more further embodiments of the present disclosure operate to generate a trigger, or use a method, in a situation where another "stand-by" (or "ready mode") signal is on and a detection or detected signal has crossed a threshold.

In accordance with at least another aspect of the present disclosure, the one or more fluorescence triggers, an auto-fluorescence triggers, NIRAF triggers, etc. or methods to control one or more devices, systems, etc. and one or more other technique(s) discussed herein may be employed to reduce the cost of at least one of manufacture and maintenance of one or more devices, systems and storage mediums by reducing or minimizing a number of optical components in an interference optical system, such as an interferometer and/or such as using other light sources including LEDs (e.g., when sensitivity is sufficient and/or meets a predetermined condition, threshold or requirement) to cut down cost.

In one or more embodiments, a double clad fiber (DCF) may be used for optical probes of multi-modality systems such as OCT, fluorescence, and/or spectroscopy. The core of DCF may be used to illuminate, and the clad of DCF may be used to collect fluorescence or backscattering from sample efficiently.

According to other aspects of the present disclosure, one or more additional devices, one or more systems, one or more methods and one or more storage mediums using, or for use with, one or more FORJs are discussed herein. Further features of the present disclosure will in part be understandable and will in part be apparent from the following description and with reference to the attached drawings.

BRIEF DESCRIPTION OF THE DRAWINGS

For the purposes of illustrating various aspects of the disclosure, wherein like numerals indicate like elements, there are shown in the drawings simplified forms that may be employed, it being understood, however, that the disclosure is not limited by or to the precise arrangements and instrumentalities shown. To assist those of ordinary skill in the relevant art in making and using the subject matter hereof, reference is made to the appended drawings and figures, wherein:

FIGS. 2A-2B are diagrams showing respective embodiments of a system which can utilize a trigger or method in accordance with one or more aspects of the present disclosure;

FIG. 11 shows a schematic diagram of an embodiment of a computer that may be used with one or more embodiments of a fiber optic rotary joint in accordance with one or more aspects of the present disclosure; and FIG. 12 shows a schematic diagram of another embodiment of a computer that may be used with one or more embodiments of a fiber optic rotary joint in accordance with one or more aspects of the present disclosure.

DETAILED DESCRIPTION OF THE PRESENT INVENTION

One or more devices, optical systems, methods and storage mediums for imaging using and/or generating a trigger for recording one or more images, and one or more embodiments of a fluorescence trigger, an auto-fluorescence trigger, a NIRAF trigger, etc. or a fluorescence, auto-fluorescence, and/or NIRAF method(s) for recording one or more images, are disclosed herein.

Figure 1:
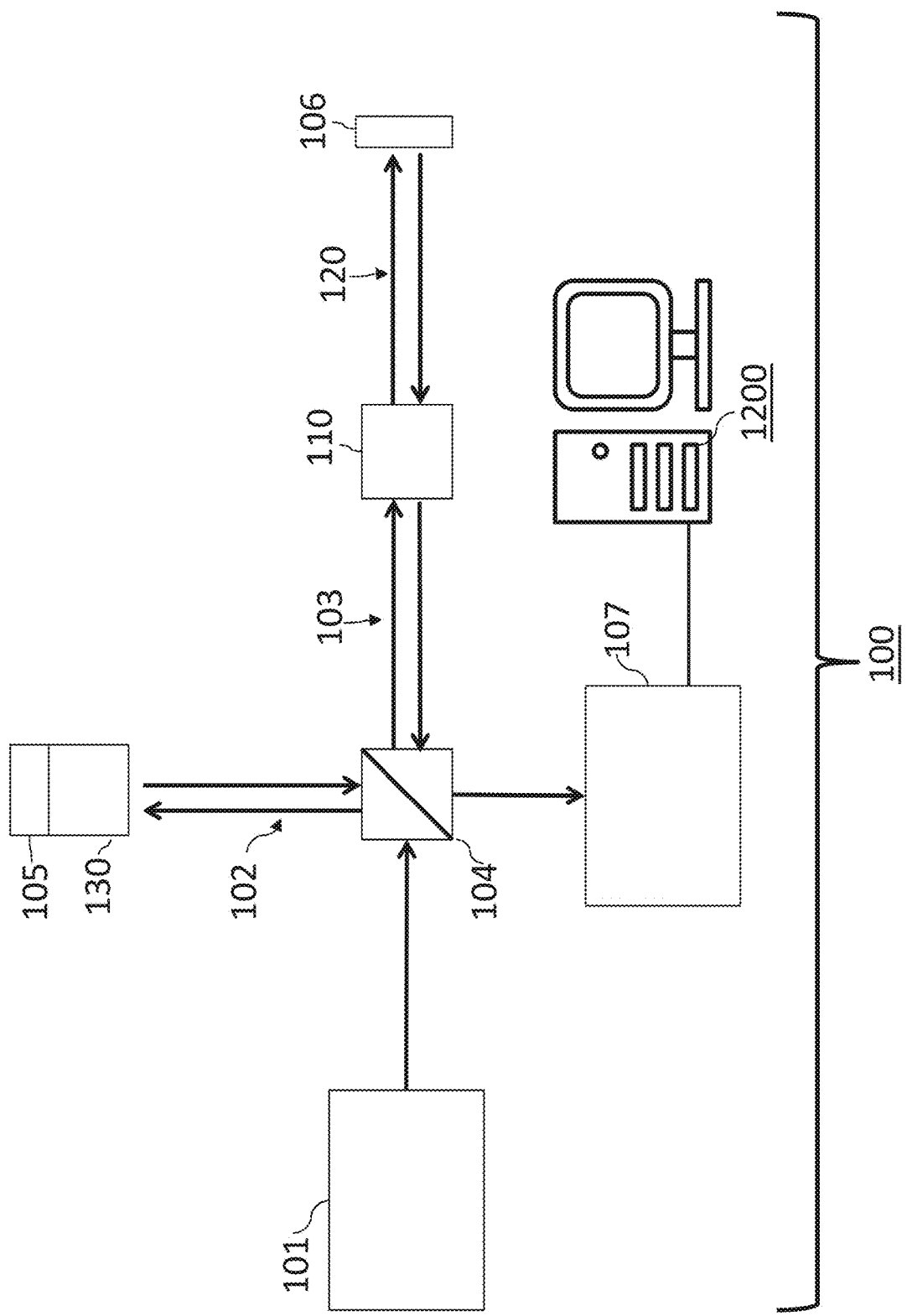
FIG. 1 is a diagram showing an embodiment of a system which can utilize a trigger or method in accordance with one or more aspects of the present disclosure.

Turning now to the details of the figures, FIG. 1 shows an OCT system 100 (as referred to herein as "system 100" or "the system 100") which operates to utilize an OCT technique with optical probe applications in accordance with one or more aspects of the present disclosure. The system 100 comprises a light source 101, a reference arm 102, a sample arm 103, a splitter 104 (also referred to herein as a "beam splitter"), a reference mirror (also referred to herein as a "reference reflection") 105, and one or more detectors 107. The system 100 may include a phase shift device or unit 130. In one or more embodiments, the system 100 may include a patient interface device or unit ("PIU") 110 and a catheter 120 (as diagrammatically shown in FIGS. 1-3), and the system 100 may interact with a sample 106 (e.g., via the catheter 120 and/or the PIU 110). In one or more embodiments, the system 100 includes an interferometer or an interferometer is defined by one or more components of the system 100, such as, but not limited to, at least the light source 101, the reference arm 102, the sample arm 103, the splitter 104 and the reference mirror 105.

The light source 101 operates to produce a light to the splitter 104, which splits the light from the light source 101 into a reference beam passing into the reference arm 102 and a sample beam passing into the sample arm 103. The beam splitter 104 is positioned or disposed at an angle to the reference mirror 105, the one or more detectors 107 and to the sample 106. The reference beam goes through the phase shift unit 130 (when included in a system, as shown in the system 100), and the reference beam is reflected from the reference mirror 105 in the reference arm 102 while the sample beam is reflected or scattered from a sample 106 through the PIU (patient interface unit) 110 and the catheter 120 in the sample arm 103. Both of the reference and sample beams combine (or recombine) at the splitter 104 and generate interference patterns. The output of the system 100 and/or the interferometer thereof is continuously acquired with the one or more detectors 107, e.g., such as, but not limited to, photodiodes or multi-array cameras. The one or more detectors 107 measure the interference or interference patterns between the two radiation or light beams that are combined or recombined. In one or more embodiments, the reference and sample beams have traveled different optical path lengths such that a fringe effect is created and is measurable by the one or more detectors 107. Electrical analog signals obtained from the output of the system 100 and/or the interferometer thereof are converted to digital signals to be analyzed with a computer, such as, but not limited to, the computer 1200, 1200' (shown in FIG. 11 or FIG. 12, respectively, discussed further below). In one or more embodiments, the light source 101 may be a radiation source or a broadband light source that radiates in a broad band of wavelengths. In one or more embodiments, a Fourier analyzer including software and electronics may be used to convert the electrical analog signals into an optical spectrum.

The light source 101 may include a plurality of light sources or may be a single light source. The light source 101 generates broadband laser lights in one or more embodiments. The light source 101 may include one or more of a laser, an organic Light-Emitting Diode (OLED), a Light-Emitting Diode (LED), a halogen lamp, an incandescent lamp, supercontinuum light source pumped by a laser, and/or a fluorescent lamp. The light source 101 may be any light source that provides light which can then be split up into at least three bands in which each band is further dispersed to provide light which then used to for spectral encoding of spatial information. The light source 101 may be fiber coupled or may be free space coupled to the other components of the system or systems discussed herein, such as, but not limited to, the system 100, the system 100', the system 100", etc.

In accordance with at least one aspect of the present disclosure, a feature of OCT systems is implemented using fiber optics. As aforementioned, one application of an OCT technique of the present disclosure is to use OCT with a catheter 120 as schematically shown in FIGS. 1-3.

FIG. 2A shows at least one embodiment of an OCT and fluorescence multi-modality system 100' in accordance with the present disclosure. One or more embodiments of an OCT and fluorescence multi-modality system may include an OCT sub-system, a fluorescence sub-system, a PIU, a catheter, blood clearance features and processing capabilities further discussed below.

Figure 2B:
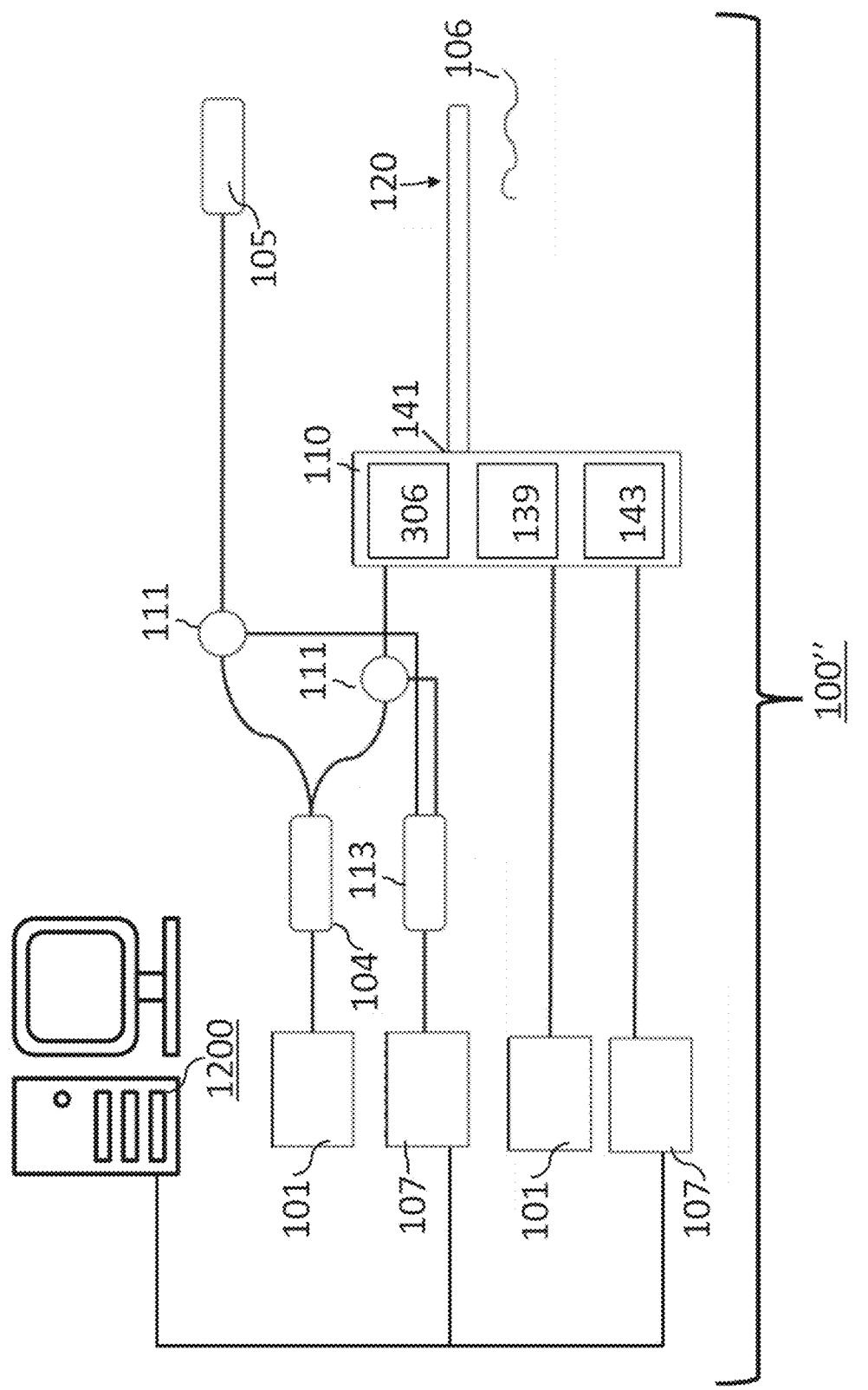
Figure 3:
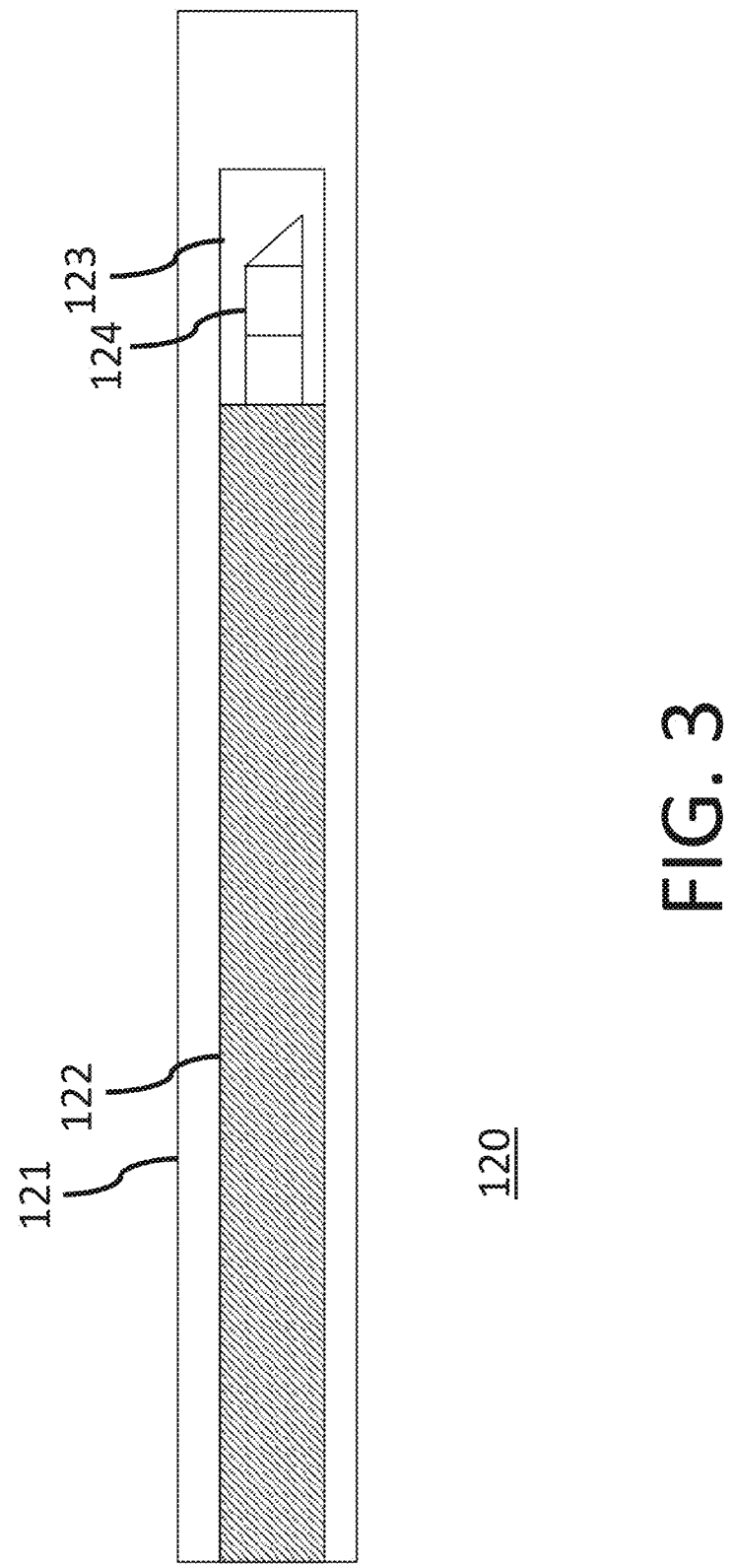
FIG. 3 is a diagram of an embodiment of a catheter that may used with at least one embodiment of a trigger or method in accordance with one or more aspects of the present disclosure.

In one or more embodiments of an OCT sub-system, an OCT light with a wavelength of around 1.3 um from a light source (e.g., a light source 101 as discussed herein) may be delivered and split into a reference arm (e.g., a reference arm 102 as discussed herein) and a sample arm (e.g., a sample arm 103 as discussed herein) with a splitter (e.g., a splitter 104 as discussed herein) (see e.g., FIG. 2A). A reference beam may be reflected from a reference mirror (e.g., a reference reflection 105 as discussed herein) in the reference arm 102 while a sample beam may be reflected and/or scattered from a sample (see e.g., the sample 106 in FIG. 2B) through a PIU (patient interface unit) (e.g., the PIU 110 as discussed herein) and a catheter or probe (e.g., a catheter or probe 120 as discussed herein) in the sample arm 103. Fibers of the PIU 110 and catheter/probe 120 may be made of a DCF (double clad fiber) in one or more embodiments. The OCT light illuminates a sample (e.g., the sample 106) through the core of the DCF, and scattered light from the sample (e.g., the sample 106) are collected and delivered back to a splitter (see e.g., the splitter 104)/circulator (see e.g., a circulator 111 as discussed herein)/detector (see e.g., the detector 107 as discussed herein, the top detector 107 of FIG. 2A, etc.) of an OCT interferometer via the PIU 110 and combined with a reference beam at a combiner (see e.g., a combiner 113 as discussed herein) and/or detector to generate interference patterns. The output of the interferometer may be detected with OCT detectors 107, such as, but not limited to, photodiodes or multi-array cameras, any other detector(s) discussed herein, and/or any other detector(s) known to those skilled in the art. Then signals may be transferred to a computer (e.g., a computer 1200, 1200' or any other computer or processor discussed herein, etc.) to perform signal processing to generate OCT images. In one or more embodiments, the interference patterns are generated in a case where the path length of the sample arm 103 matches the path length of the reference arm 102 to within the coherence length of the light source 101.

In one or more embodiments of a fluorescence sub-system, an excitation light with a wavelength of 0.633 um from a fluorescence light source (see e.g., the fluorescence light source 101 discussed herein) may be delivered to the sample (e.g., the sample 106) through the PIU 110 and the catheter/probe 120 (see e.g., FIG. 2A). In one or more embodiments, the PIU 110 comprises a free space beam combiner so that the excitation light couples into the common DCF with OCT. The excitation light is illuminated to the sample from a distal end of the optical probe in the catheter 120. In one or more embodiments, the sample emits fluorescence or auto-fluorescence with broadband wavelengths of 0.633-0.90 um. The fluorescence or auto-fluorescence may be collected with the catheter/probe 120 and delivered to a fluorescence detector 107 via the PIU 110 where the fluorescence detector 107 is configured to detect light having a wavelength of between 633 and 900 nm. In other embodiments of a fluorescence sub-system, an excitation light with a wavelength of between 500-700 nm (e.g., 532 nm) from a fluorescence light source (e.g., the fluorescence light source 101) may be delivered to the sample (e.g., the sample 106) through the PIU 110 and the catheter/probe 120. In this embodiment, an exogenous dye such as methylene blue (also known as methylthionium chloride) may be provided into the patient's lumen or a lumen of the target, object, or sample 106. The fluorescence may be collected with the catheter/probe 120 and delivered to a fluorescence detector 107 via the PIU 110, where the fluorescence detector 107 is configured to detect light having a wavelength of between 600-750 nm.

Preferably, in one or more embodiments of the present disclosure, a change of the intensity of the fluorescence or auto-fluorescence from blood cells, a predetermined object, a target, a sample, etc. are monitored and utilized to generate pullback and/or record triggers.

Figure 7:
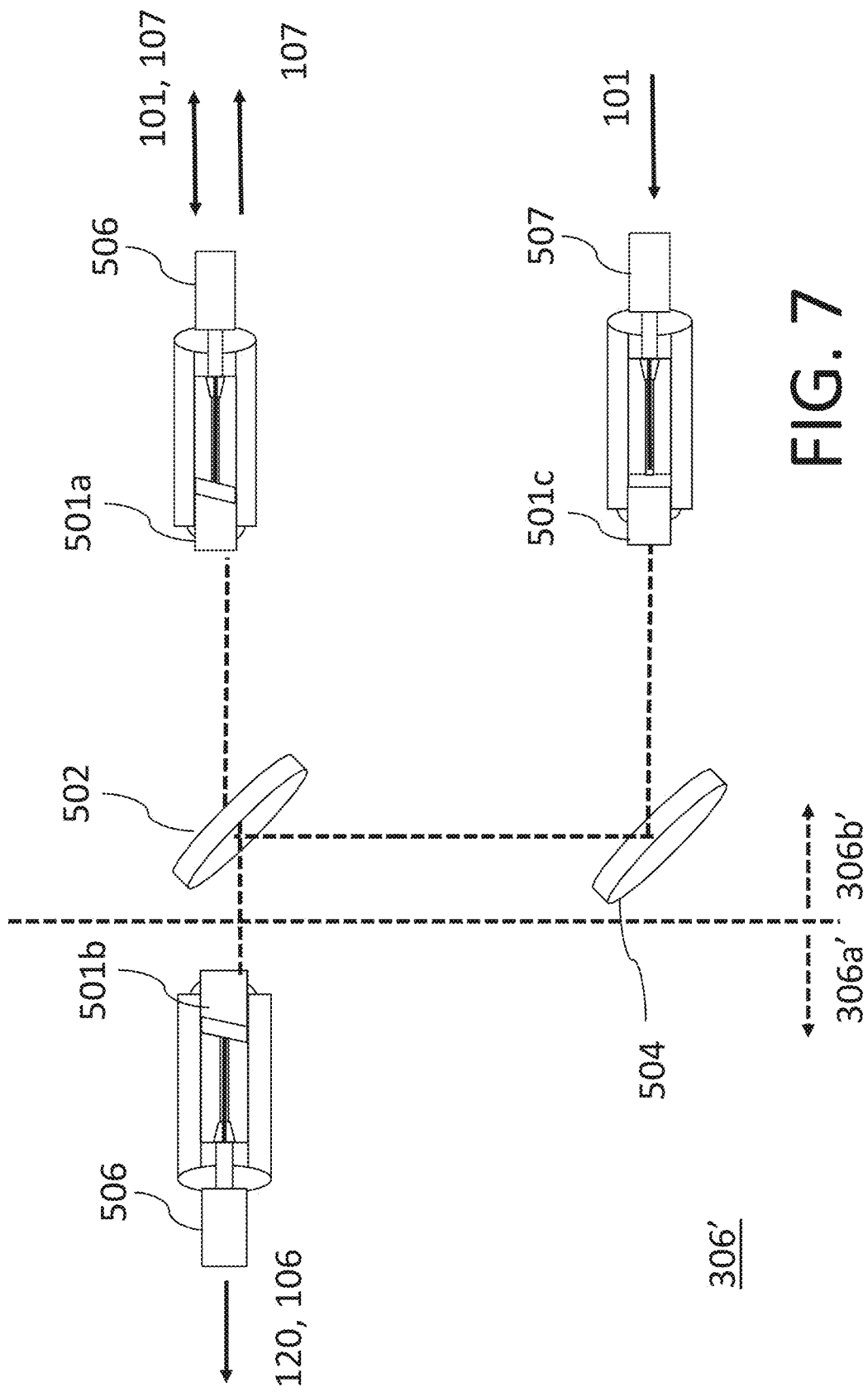
FIG. 7 is a diagram showing at least one embodiment of a free space beam combiner that may be used in at least one embodiment of a fiber optic rotary joint using a trigger or a method in accordance with one or more aspects of the present disclosure.

In one or more embodiments of the present disclosure, a PIU (e.g., the PIU 110) may comprise a free space beam combiner (e.g., a free space beam combiner 143 as shown in FIG. 2B), a FORJ (Fiber Optic Rotary Joint) (e.g., a FORJ 306 as discussed herein and shown in at least FIGS. 2B and 4-5, a FORJ 306' as shown in FIG. 7, etc.), a rotational motor and translation motorized stage (see e.g., portion 139 of PIU 110 as shown in FIG. 2B), and a catheter connector (see e.g., portion 141 of the PIU 110 as discussed herein and as shown in FIG. 2B).

Preferably, in one or more embodiments, the FORJ 306, 306', etc. allows uninterrupted transmission of an optical signal while rotating the double clad fiber on the left side along the fiber axis in one or more embodiments, such as the embodiments shown in FIGS. 4-5 (further discussed below). The FORJ 306, 306', etc. has a free space optical beam coupler to separate a rotor 306a, 306a' and a stator 306b, 306b' in one or more embodiments. The rotor 306a, 306a' (also referred to herein as a rotator) may comprise a double clad fiber with a lens to make collimated beam. The rotor 306a, 306a' operates to be connected to the optical probe, and the stator 306b, 306b' operates to be connected to the optical sub-systems (e.g., the OCT sub-system, the fluorescence sub-system, etc.). In one or more embodiments using the rotational motor (see e.g., portion 139 of PIU 110 as shown in FIG. 2B), the rotational motor (see e.g., portion 139 of PIU 110 as shown in FIG. 2B) delivers the torque to the rotor 306a, 306a'. Also, the translation motorized stage (see e.g., portion 139 of PIU 110 as shown in FIG. 2B) may be used for a pullback. A catheter connector (see e.g., portion 141 of the PIU 110 as discussed herein and as shown in FIG. 2B) operates to be connected to the catheter/probe 120.

The free space beam combiner (e.g., a free space beam combiner 143 as shown in FIG. 2B) preferably has dichroic filters to separate different wavelength lights (for example, OCT, excitation light and Raman and fluorescence or auto-fluorescence lights, etc.—see e.g., FIG. 5; see also, discussion of FIG. 4 below). In one or more embodiments, the beam combiner (e.g., a free space beam combiner 143 as shown in FIG. 2B) also may comprise low-pass filters or band-pass filters in front of the Raman and fluorescence or auto-fluorescence channel to eliminate excitation light because of minimized excitation light noises at the fluorescence detector. The cut-off wavelength of the filter (low-pass or band-pass) is selected around from 645 to 670 nm. In one or more embodiments, the free space beam combiner 143 may be included in one or more of the other components of the PIU 110, such as, but not limited to, the FORJ 306.

FIG. 2B shows at least one embodiment of a system 100" which includes OCT and fluorescence sub-systems. In one or more embodiments, the OCT sub-system includes a light source, such as the light source 101, a splitter (such as the splitter 104; another type of deflecting or deflection device discussed below may be used in place of the splitter 104), one or more circulators 111, a reference reflection (such as the reference reflection 105), a combiner (such as the combiner 113), and at least one detector (such as the at least one detector 107). The OCT sub-system may be connected to, and include, a patient interface unit, such as the PIU 110, and the catheter 120 to expose a sample, such as the sample 106, to light and receive information in response thereto. In one or more embodiments, the fluorescence sub-system may include a light source for fluorescence (such as the second or lower light source 101 shown in FIG. 2B) and at least one detector (such as the second or lower at least one detector 107 shown in FIG. 2B). The fluorescence sub-system, including, but not limited to, the second light source 101 and the second at least one detector 107, may also be connected to (see FIG. 2B), and/or include, a patient interface unit, such as the PIU 110, and the catheter 120 to expose a sample, such as the sample 106, to fluorescent light and receive information in response thereto. For example, in at least one embodiment, an OCT light with a wavelength of around 1.3 um from a light source (such as the light source 101 of the OCT sub-system) is delivered and split into a reference arm (e.g., the reference arm 102) and a sample arm (e.g., the sample arm 103) with a splitter (e.g., the splitter 104). A reference beam is reflected from a reference mirror (e.g., the reference reflection 105) in the reference arm (e.g., the reference arm 102) while a sample beam is reflected or scattered from a sample through a PIU (patient interface unit) (such as the PIU 110) and a catheter (e.g., the catheter/probe 120) in the sample arm (e.g., the sample arm 103). Both beams combine at a combiner (e.g., the splitter 104 in FIG. 1, the combiner shown in FIG. 2A, the combiner 113 in FIG. 2B, etc.) and generate interference patterns. The output of the interferometer is detected with detectors (e.g., the at least one detector 107 shown in FIG. 1, the detectors shown in FIG. 2A, the at least one detector 107 of the OCT sub-system shown in FIG. 2B, etc.) such as photodiodes or multi-array cameras. Then signals are transferred to a computer (e.g., the computer 1200 as shown in FIGS. 1-2B and 11, the computer 1200' of FIG. 12, any other computer discussed herein, etc.) to perform signal processing. In one or more embodiments, the interference patterns are generated in a case where the path length of the sample arm (e.g., the sample arm 103) matches that of the reference arm (e.g., the reference arm 102) to within the coherence length of the light source (e.g., the light source 101 of FIG. 1, the OCT light source of FIG. 2A (see top light source 101 in FIG. 2A), the light source 101 of the OCT sub-system of FIG. 2B (see top light source 101 in FIG. 2B), etc.).

An excitation light with a wavelength (e.g., any predetermined wavelength visible to infrared (IR)), for example, 0.633 um from a light source (e.g., the fluorescence light source (see lower light source 101 in FIG. 2A) of FIG. 2A, the light source 101 of the fluorescence sub-system of FIG. 2B, etc.) is delivered to the sample (e.g., the sample 106) through the PIU (e.g., the PIU 110) and the catheter (e.g., the catheter/probe 120). The sample (e.g., the sample 106) emits fluorescence or auto-fluorescence light with broadband wavelengths of, for example, 0.633 um-0.80 um by the excitation light. The fluorescence or auto-fluorescence light is collected with the catheter (e.g., the catheter/probe 120 of FIG. 2A, the catheter/probe 120 of FIG. 2B, etc.) and delivered to detectors (e.g., the fluorescence detector (see e.g., bottom or lower detector 107) of FIG. 2A, the detector(s) 107 of the fluorescence sub-system of FIG. 2B, etc.) via the PIU (e.g., the PIU 110). Other wavelengths, in the visible and NIR are also contemplated.

FIG. 3 shows an embodiment of the catheter 120 including a sheath 121, a coil 122, a protector 123 and an optical probe 124. As shown schematically in FIGS. 1-2B, the catheter 120 preferably is connected to the PIU 110 to spin the coil 122 with pullback (e.g., at least one embodiment of the PIU 110 operates to spin the coil 122 with pullback). The coil 122 delivers torque from a proximal end to a distal end thereof (e.g., via or by a rotational motor in the PIU 110). In one or more embodiments, the coil 122 is fixed with/to the optical probe 124 so that a distal tip of the optical probe 124 also spins to see an omnidirectional view of a biological organ, sample or material being evaluated, such as, but not limited to, hollow organs such as vessels, a heart, etc. For example, fiber optic catheters and endoscopes may reside in the sample arm (such as the sample arm 103 as shown in FIG. 1) of an OCT interferometer in order to provide access to internal organs, such as intravascular images, gastrointestinal tract or any other narrow area, that are difficult to access. As the beam of light through the optical probe 124 inside of the catheter 120 or endoscope is rotated across the surface of interest, cross-sectional images of one or more samples are obtained. In order to acquire three-dimensional data, the optical probe 124 is simultaneously translated longitudinally during the rotational spin resulting in a helical scanning pattern. This translation is most commonly performed by pulling the tip of the probe 124 back towards the proximal end and therefore referred to as a pullback.

The catheter 120, which, in one or more embodiments, comprises the sheath 121, the coil 122, the protector 123 and the optical probe 124 as aforementioned (and as shown in FIG. 3), preferably is connected to the PIU 110. In one or more embodiments, the optical probe 124 may comprise an optical fiber connector, an optical fiber and a distal lens. The optical fiber connector may be used to engage with the PIU 110. The optical fiber preferably operates to deliver light to the distal lens. The distal lens preferably operates to shape the optical beam and to illuminate light to the sample (e.g., the sample 106 discussed above), and to collect light from the sample (e.g., the sample 106 discussed above) efficiently.

As aforementioned, in one or more embodiments, the coil 122 delivers torque from a proximal end to a distal end thereof (e.g., via or by a rotational motor in the PIU 110). Preferably, there is a mirror at the distal end so that the light beam is deflected outward. In one or more embodiments, the coil 122 is fixed with/to the optical probe 124 so that a distal tip of the optical probe 124 also spins to see an omnidirectional view of a biological organ, sample or material being evaluated, such as, but not limited to, hollow organs such as vessels, a heart, etc. In one or more embodiments, the optical probe 124 may include a fiber connector at a proximal end, a double clad fiber and a lens at distal end. The fiber connector operates to be connected with the PIU 110. The double clad fiber preferably operates to transmit & collect OCT light through the core and to collect Raman and/or fluorescence from a sample (e.g., the sample 106 discussed above) through the clad. The lens may be used for focusing and collecting light to and/or from the sample (e.g., the sample 106 discussed above). In one or more embodiments, the scattered light through the clad is relatively higher than that through the core because the size of the core is much smaller than the size of the clad.

In at least one embodiment, there is a mirror (e.g., mirror 504 of FIGS. 4 and 7 as discussed below; see also, the similarly situated or positioned mirror 504 of FIG. 5) at the distal end so that the light beam is deflected outward. In at least one embodiment, the optical probe 124 comprises a fiber connector at a proximal end, a double clad fiber and a lens at a distal end. The fiber connector may be connected with the PIU 110. The double clad fiber (see e.g., double clad fiber 506 of FIGS. 4 and 7 as discussed below; see also, the similarly situated or positioned double clad fiber 506 of FIG. 5) is used to deliver both OCT and fluorescence lights. The lens (see e.g., GRIN lens 501*b* shown in FIGS. 4 and 7 as discussed below; see also, the similarly situated or positioned lens 501*b* as shown in FIG. 5) is used for focusing and collecting lights to and/or from the sample (e.g., the sample 106).

In one or more embodiments, the patient user interface 110 may comprise or include a connection component (or interface module), such as a rotary junction (e.g., the rotary junction 306 and/or 306' as shown schematically in FIGS. 2B, 4-5 and 7, another rotary junction discussed herein, etc.), to connect one or more components, such as one or more components of a probe (e.g., a catheter 120 (see e.g., FIGS. 1-3), the catheter/probe 120 of FIG. 2A, etc.), a needle, a capsule, a patient interface unit (e.g., the patient interface unit 110), etc., to one or more other components, such as, an optical component, a light source (e.g., the light source 101), a deflection section (e.g., such as the deflection or deflected section, which is a component that operates to deflect the light from the light source to the interference optical system, and then send light received from the interference optical system towards the at least one detector; a deflection or deflected section that includes at least one of: one or more interferometers, a circulator, a beam splitter, an isolator, a coupler, a fusion fiber coupler, a partially severed mirror with holes therein, and a partially severed mirror with a tap; etc.), the sample arm 102, a motor that operates to power the connection component and/or the patient user interface 110, etc. For example, when the connection member or interface module is a rotary junction, preferably the rotary junction operates in the same or similar fashion as the rotary junction 306 discussed herein). In one or more other embodiments, the rotary junction may be at least one of: a contact rotary junction, a lenseless rotary junction, a lens-based rotary junction, or other rotary junction known to those skilled in the art.

In at least one embodiment, the PIU 110 may include a FORJ (such as the rotary joint 306, 306' discussed herein), a rotational motor and translation motorized stage (see e.g., portion 139 of PIU 110 as shown in FIG. 2B), and a catheter connector (see e.g., portion 141 of the PIU 110 as shown in FIG. 2B). The FORJ (such as the rotary joint 306, 306' discussed herein) allows uninterrupted transmission of an optical signal while rotating the double clad fiber (e.g., the DCF 506) along the fiber axis. The FORJ (such as the rotary joint 306, 306' discussed herein) has a free space optical beam combiner consisting of a rotor and stator (see e.g., rotor 306*a* and stator 306*b* as shown in FIG. 4 and the similarly structured rotor 306*a* and stator 306*b* as shown in FIG. 5 as discussed herein; see also, rotor 306*a'* and 306*b'* as shown in FIG. 7 and as discussed further below). FIG. 4 shows a configuration of a free space beam combiner and FORJ in accordance with at least one embodiment of the present disclosure. In an OCT and fluorescence system (such as the system 100' as shown in FIG. 2A, such as the system 100" as shown in FIG. 2B, etc.), the stator (e.g., the stator 306*b* of FIG. 4, the similarly situated and/or structured stator 306*b* of FIG. 5, the stator 30*b'* of FIG. 7 as discussed below, etc.) comprises at least two (2) optical fibers for OCT and excitation (see e.g., single mode fiber 507*a* of FIG. 4 that operates for OCT light source delivery and light detection or the similarly situated and/or structured single mode fiber 507*a* of FIG. 5; single mode fiber 507*b* of FIG. 4 that operates to work with the excitation light source 107 (e.g., fluorescence light source 101 of the fluorescence sub-system or portion of system 100' of FIG. 2A; light source 101 of the fluorescence sub-system or portion of system 100" of FIG. 2B; etc.) or the similarly situated and/or structured single mode fiber 507*b* of FIG. 5; etc.). Each fiber has a lens at the beam combiner side of each fiber (e.g., the single mode fiber 507*a* is connected to a GRIN lens 501*a* as shown in FIG. 4; the multi-mode fiber 508 is connected to a GRIN lens 501*d* as shown in FIG. 4; the single mode fiber 507*b* is connected to a GRIN lens 501*c* as shown in FIG. 4; see also, the similarly situated and/or structured fibers and lens pairings as shown in FIG. 5; etc.). The rotor (e.g., the rotor 306*a* of FIG. 4; the similarly situated and/or structured rotor 306*a* of FIG. 5; etc.) is made of a double clad fiber (e.g., the double clad fiber 506) with a fiber connection at the catheter (e.g., the catheter 120) side and a lens (e.g., a GRIN lens 501*b* as shown in FIG. 4; a similarly situated and/or structured lens 501*b* of FIG. 5; etc.) at the beam combiner side. Then, the fiber connector of the rotor (e.g., the rotor 306*a*) is connected to the optical probe (e.g., the optical probe 124 via the catheter 120 as shown in FIGS. 3-5; see also, connection structure of FIG. 7 discussed below), and the stator (e.g., the stator 306*b* of FIG. 4; the similarly situated and/or structured stator 306*b* of FIG. 5; etc.) is connected to the optical sub-systems (as shown schematically in FIGS. 4-5; see also, structure shown in FIG. 7). For example, in at least one embodiment as best seen schematically in FIG. 4, the single mode fiber 507*a* is connected to the OCT light source (e.g., the light source 101) and the detection elements (e.g., the at least one detector 107) of the OCT sub-system, the multi-mode fiber 508 is connected to the fluorescence detection elements (e.g., the at least one detector 107) of the fluorescence sub-system), and the single mode fiber 507*b* is connected to the excitation light source (e.g., the light source 101) of the fluorescence sub-system. As shown in at least the embodiment of FIG. 5, a multi-mode fiber 508 (situated and/or structured similarly to the multi-mode fiber 508 of FIG. 4) may be connected to the Raman and/or fluorescence detection elements (e.g., the at least one detector 107) of the fluorescence sub-system) of the Raman and fluorescence or auto-fluorescence channel. The rotational motor (e.g., the rotational motor 139) delivers the torque to the rotor (e.g., the rotor 306*a*; the similarly situated and/or structured rotor 306*a* of FIG. 5; etc.). Also, the translation motorized stage may be used for a pullback such that the beam is scanned inside the lumen sample in a helical manner. The catheter connector (e.g., the catheter connector 141 as shown schematically in FIG. 2B, which may be used similarly in the system 100' of FIG. 2A in one or more embodiments) is connected to the catheter (e.g., the catheter/probe 120).

Figure 4:
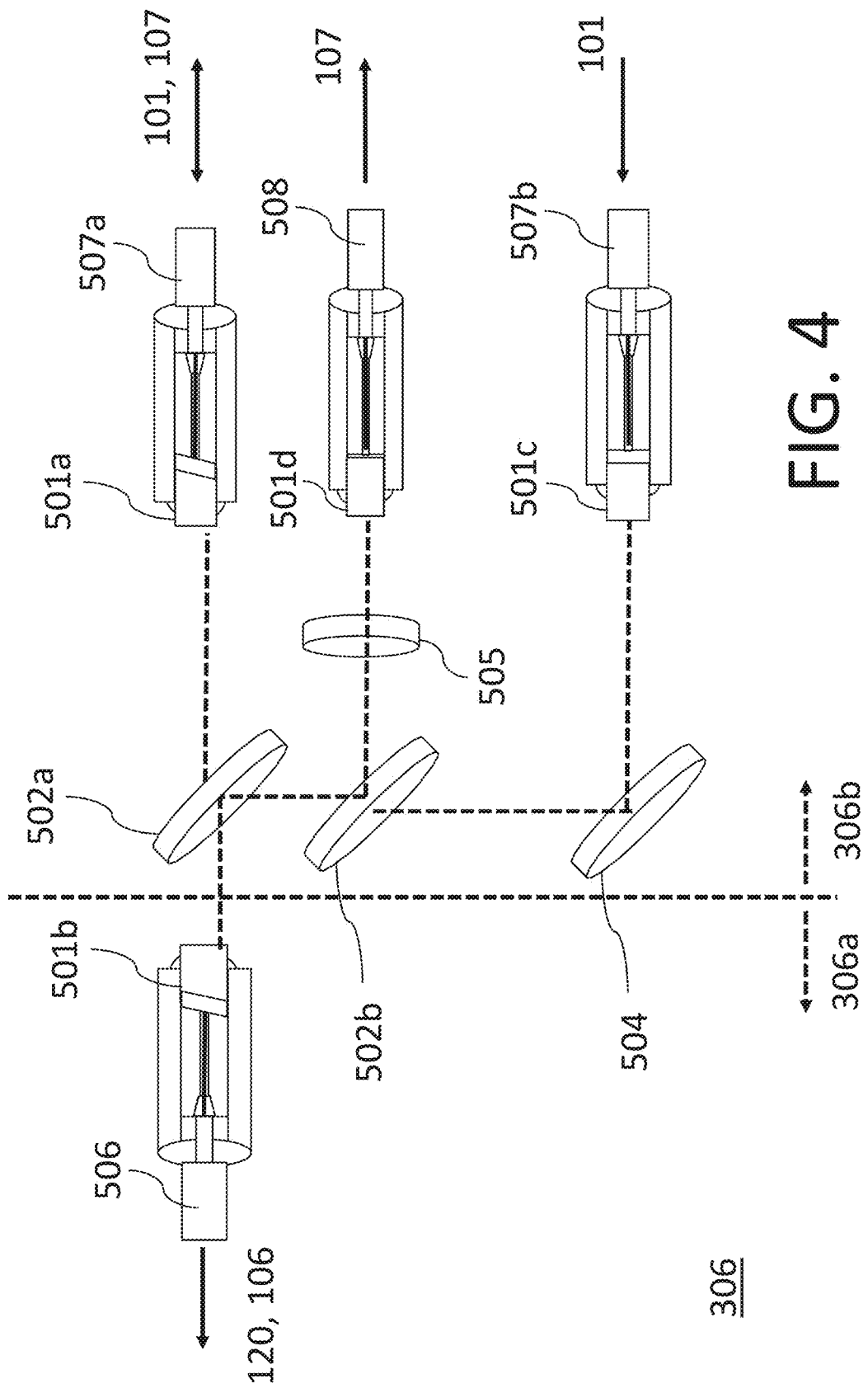
FIGS. 4-5 are diagrams showing respective embodiments of a fiber optic rotary joint that may be used with at least one embodiment of a trigger or method in accordance with one or more aspects of the present disclosure.
Figure 5:
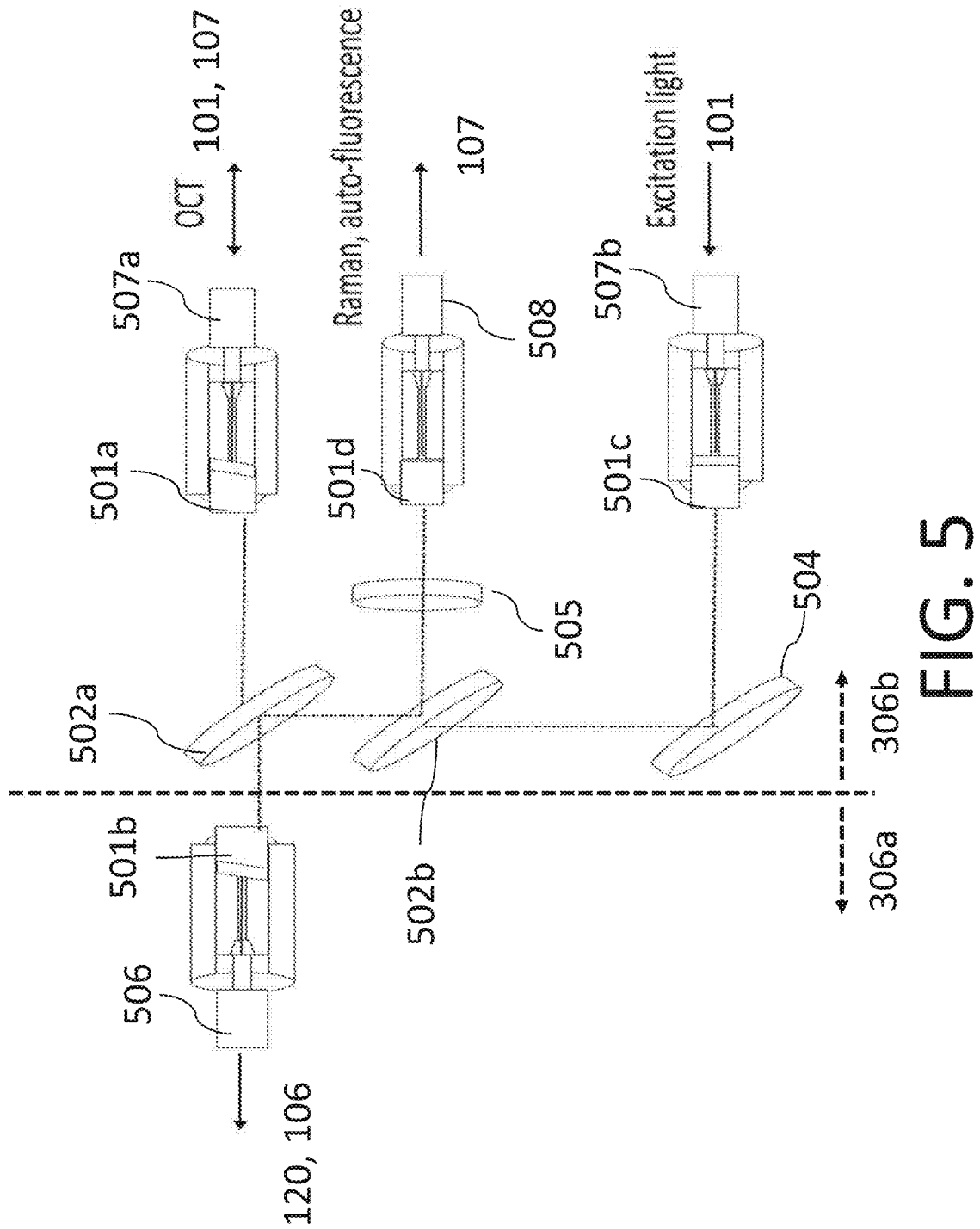

As best seen in FIG. 4, OCT light is collimated with a GRIN lens 501*a* from single mode fiber 507*a*. The collimated OCT light couples into the core of the double clad fiber 506 (of rotor 306*a*) via a dichroic filter 502*a* and a GRIN lens 501*b*. Also, the back scattered OCT light from the sample (e.g., the sample 106) goes back to the rotor 306*a* (via the catheter 120). The light may be collimated with the GRIN lens 501*b* and may couple into the single mode fiber. In one or more embodiments, the magnification is approximately or about 1, or is 1, in order to couple fiber efficiently because OCT light is delivered with reversible paths (for example, from stator 306*b* to rotor 306*a* and from rotor 306*a* to stator 306b). Coupling efficiency is improved or maximized when having the magnification be approximately or about 1, or be 1.

One or more embodiments of the present disclosure may be used with one or more fiber optic rotary joints, fiber optic rotary joint features, and methods of using and manufacturing same as disclosed in U.S. Pat. Pub. No. 2018/0348439, published Dec. 6, 2018, which is incorporated by reference herein in its entirety.

One or more embodiments may couple OCT and excitation channels into a single core of a double clad fiber in a rotary junction as disclosed in U.S. Pat. Pub. No. 2018/0348439, published Dec. 6, 2018, which is incorporated by reference herein in its entirety.

In one or more embodiments, excitation light of 0.633 um wavelength from the single mode fiber 507b may be converged with a GRIN lens 501c. The light may be focused at the middle, or at a predetermined position of the optical path to the GRIN lens 501b, and then the light is coupled into mostly the core of the double clad fiber 506 with the GRIN lens 501b, as shown in FIG. 4 and as further discussed in U.S. Pat. Pub. No. 2018/0348439, published Dec. 6, 2018, which is incorporated by reference herein in its entirety.

In one or more embodiments, fluorescence light from mostly the cladding of the double clad fiber 506 may be delivered through GRIN lens 501b, as discussed in U.S. Pat. Pub. No. 2018/0348439, published Dec. 6, 2018, which is incorporated by reference herein in its entirety.

In at least one embodiment, the OCT light may be collimated with GRIN lens 501a and GRIN lens 501b, respectively, in order to achieve less sensitivity when aligning the distances between GRIN lens 501a and GRIN lens 501b. The excitation light, which, in at least one embodiment, is a shorter wavelength than the wavelength of the OCT light, may converge and may be focused by GRIN lens 501c to an intermediate focus, and then may be coupled substantially (e.g., 100%, about 100%, 90%, 80%, about 90% to about 100%, etc.) into the core of the double clad fiber 506 as discussed in U.S. Pat. Pub. No. 2018/0348439, published Dec. 6, 2018, which is incorporated by reference herein in its entirety. In this configuration, the excitation light couples efficiently into the core of double clad fiber 506, and also the alignment of GRIN lens 501c and single mode fiber 507b becomes easier because GRIN lens 501c and single mode fiber 507b are assembled separately with the assembly of GRIN lens 501b. One or more embodiments of fabrication processes are discussed below.

In some embodiments, the excitation light may be a shorter wavelength than the wavelength of the OCT light. For example, the excitation light is at least 20%, 30%, or 40% shorter than the wavelength of the OCT light. Thus, with visible and NIR excitation, the wavelength of the excitation light is, in an exemplary embodiment, at least 400 nm shorter than the wavelength of the OCT light. In one or more alternative embodiments, the excitation light may have a greater wavelength than the wavelength of the OCT light.

In one or more embodiments, as best seen in FIG. 4, dichroic filter 502a is used for separating OCT light from the rest of excitation and fluorescence light. Dichroic filter 502b is used for a separation of the excitation and fluorescence light. The mirror 504 is used to reflect the excitation light. The long-pass filter 505 may be used to filter out back-reflection and/or stray light of excitation light.

Also, the optical path lengths of OCT (Loct), fluorescence (Lfl) and excitation (Lex) light are designed, in at least one embodiment, with the following condition: Loct<Lfl<Lex. In one or more embodiments, it is preferred to have the OCT optical path length be as short as possible to improve and/or maximize coupling efficiency. It may be difficult to achieve a collimated beam that has a beam waist far (in one or more embodiments, a far beam waist depends on the lens size and quality; for example, in one or more embodiments, >50 mm beam waist may be far whereas, in other embodiments, >50 mm beam waist may not be far) from a collimator lens. In at least one embodiment, excitation light may be focused at the middle, or at a predetermined location, of the optical path so a longer optical path length may be designed as discussed in U.S. Pat. Pub. No. 2018/0348439, published Dec. 6, 2018, which is incorporated by reference herein in its entirety. Fluorescence light may be diverged (or diverges) and may have a large diameter beam, so, in one or more embodiments, it is preferred to shorten the optical path length of fluorescence light.

In at least one embodiment, wavelengths of excitation light with 350-850 nm and fluorescence light with 400-1200 nm may be chosen based on targeted markers. Collagen and/or elastin with an excitation wavelength of 350-400 nm and fluorescence or auto-fluorescence of 400-500 nm are utilized. Lipid and/or fat may be detected with the excitation wavelength of 550-650 nm and fluorescence or fluorescence wavelength of 600-850 nm. ICG (Indocyanine green) marker is used with excitation light with 600-800 nm wavelength and fluorescence light with 750-1200 nm. Any other fluorescence or auto-fluorescence marker(s) and fluorescence or auto-fluorescence dye(s) may be utilized with one or more embodiments of the present disclosure. For example, methylene blue (also known as methylthionium chloride) may be used in one or more fluorescence embodiments. Preferably, methylene blue marker is used with excitation light with 500-700 nm wavelength and fluorescence light with 600-750 nm.

When the blood is surrounded around, or surrounds, the catheter, low fluorescence or auto-fluorescence from the blood cells are detected. Then, when the blood cells are cleared by flushing media, such as, but not limited to, contrast agents, saline, and/or dextran, the fluorescence or auto-fluorescence signal intensities change because the flushing media is transparent, substantially transparent, or relatively transparent (e.g., less fluorescence or auto-fluorescence than that of the blood cells) and has less fluorescence or auto-fluorescence. The excitation light can go through the flushing media but the blood cells reduce the transmission of the excitation light due to the scattering properties, so when there are higher fluorescence or auto-fluorescence samples outside of the blood cells (in other words, when the blood cells are flushed or cleared away so that the excitation light may reach the samples more efficiently), the fluorescence or auto-fluorescence signal intensities are elevated. Also, if there are no fluorescence or auto-fluorescence samples outside of the blood cells, the fluorescence or auto-fluorescence signal intensities drop.

Figure 6:
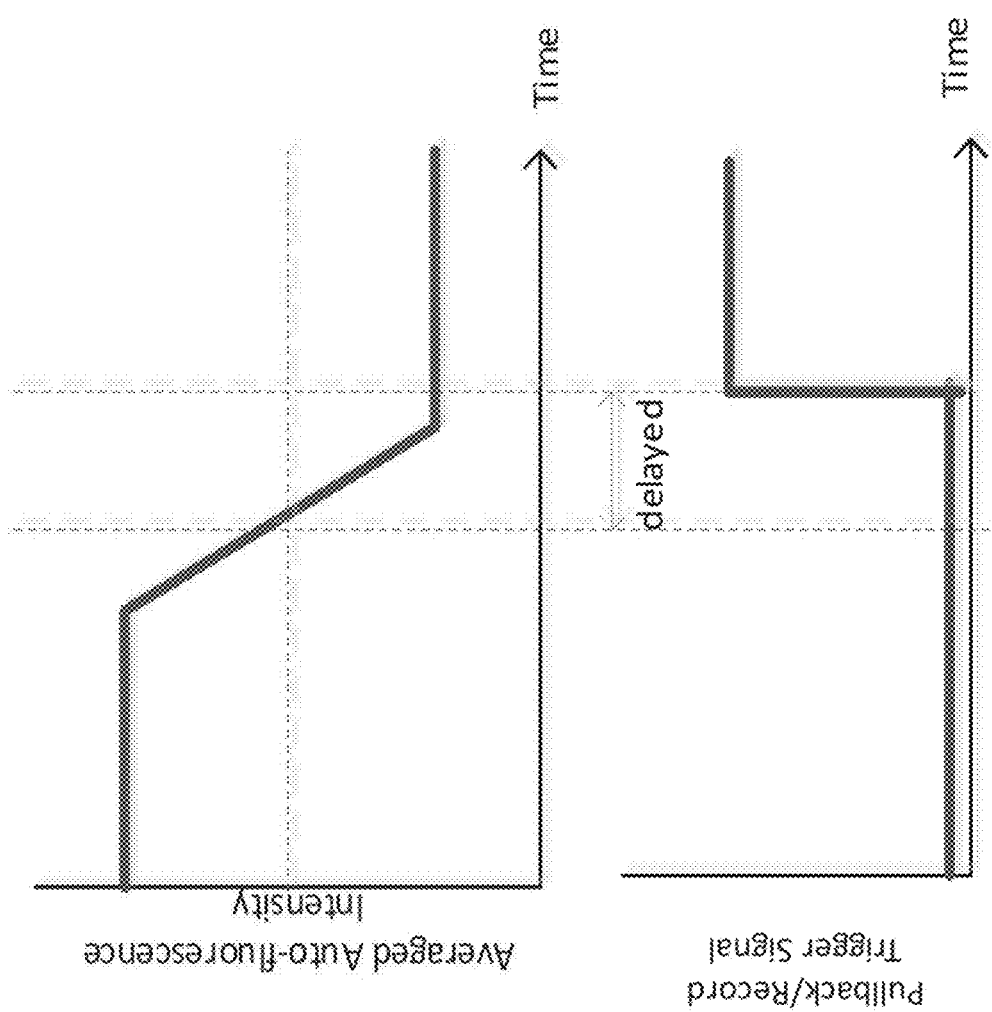
FIG. 6 includes graphs showing an example of a time sequence to generate a trigger or use a method for recording images in accordance with one or more aspects of the present disclosure.
Figure 8A:
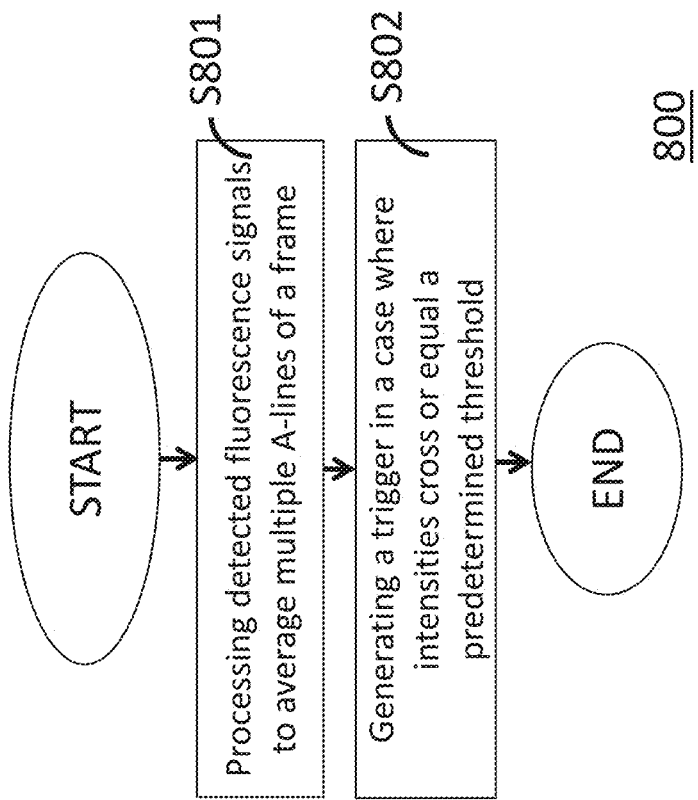
FIG. 8A is a flow chart showing at least one embodiment of a method for processing detected fluorescence or auto-fluorescence signals in accordance with one or more aspects of the present disclosure.

In accordance with at least one aspect of the present disclosure and as aforementioned, one or more methods for processing detected fluorescence or auto-fluorescence signals and/or for processing one or more triggers (e.g., fluorescence triggers, auto-fluorescence triggers, NIRAF triggers, etc.) are provided herein. FIG. 8A illustrates a flow chart of at least one embodiment of a method for processing detected fluorescence or auto-fluorescence signals. Preferably, the method(s) may include one or more of the following: (i) processing detected fluorescence or auto-fluorescence signals to average multiple A-lines of a frame (see step S801 of FIG. 8A); and (ii) generating a trigger for pullback and/or for recording image(s) in a case where intensities (e.g., fluorescence intensities, auto-fluorescence intensities, NIRAF intensities, etc.) cross or equal a predetermined threshold (see step S802 in FIG. 8A). One or more embodiments of such method(s) may further include waiting for a predetermined delay before generating, or to generate, the trigger (see e.g., the delay shown in FIG. 6, the delay shown in FIGS. 9A and 9B, the delay shown in FIG. 10, etc.).

Detected fluorescence or auto-fluorescence signals may be processed to average multiple A-lines of a frame using the following equation (1):

$$aveF = \frac{\sum_{A\text{-}line} Autofluorescence}{N}, \qquad (1)$$

where AF is a detected fluorescence or auto-fluorescence signal by a data acquisition unit, apparatus or system (hereinafter referred to as "DAQ"), N is a number of A-lines per frame, and aveAF is an average of fluorescence or auto-fluorescence per frame. In one or more embodiments, there may be multiple DAQ's used in a system, such as, but not limited to, DAQ1 (for example, DAQ1 127 for the OCT sub-system shown in system 100' in FIG. 2A) and DAQ2 (for example, DAQ2 128 for the fluorescence sub-system shown in system 100' in FIG. 2A).

Signals with at least A-lines with a frame are averaged in order to see an omnidirectional view of the inner surface of a target object or sample, such as, but not limited to, hollow vessels. Such a step operates to reduce or prevent generation of a trigger with a partial blood clearance, and also operates to reduce the influence of noises.

Figure 8B:
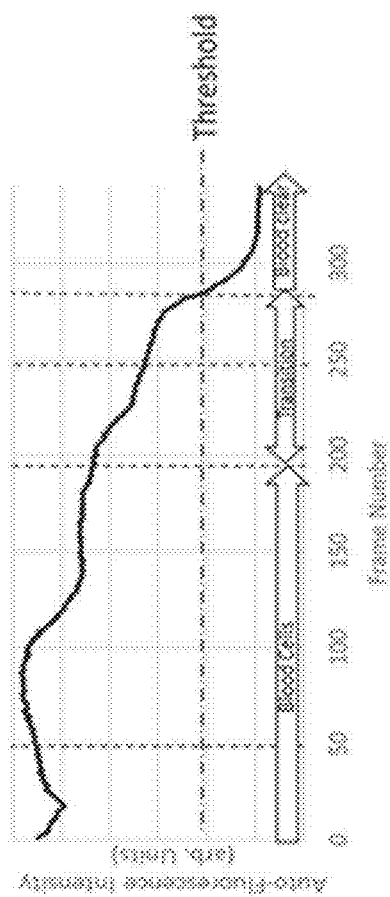
FIGS. 8B and 8C are a graph of a frame number against a fluorescence intensity or an auto-fluorescence intensity and numbered frame images of experimental results, respectively, using a trigger or method in accordance with one or more aspects of the present disclosure.

When the detected intensities cross (or in one or more embodiments, equal or cross) the predetermined threshold (see e.g., the set, predetermined, user defined, etc. threshold of FIG. 8B), the system (e.g., the system 100, the system 100', the system 100", any other system discussed herein, etc.) generates a trigger for pullback and/or record imaging (e.g., recording image(s)). The system (e.g., the system 100, the system 100', the system 100", any other system discussed herein, etc.) also may make a predetermined delay to generate the trigger as aforementioned (for example, the delay shown in FIG. 6, the delay shown in FIGS. 9A and 9B, the delay shown in FIG. 10, etc.). In one or more embodiments, the predetermined delay is determined to have, or defined such that the system (e.g., the system 100, the system 100', the system 100", any other system discussed herein, etc.) has, proper time to flush blood (or any other predetermined or target/set substance) completely.

Figure 8C:
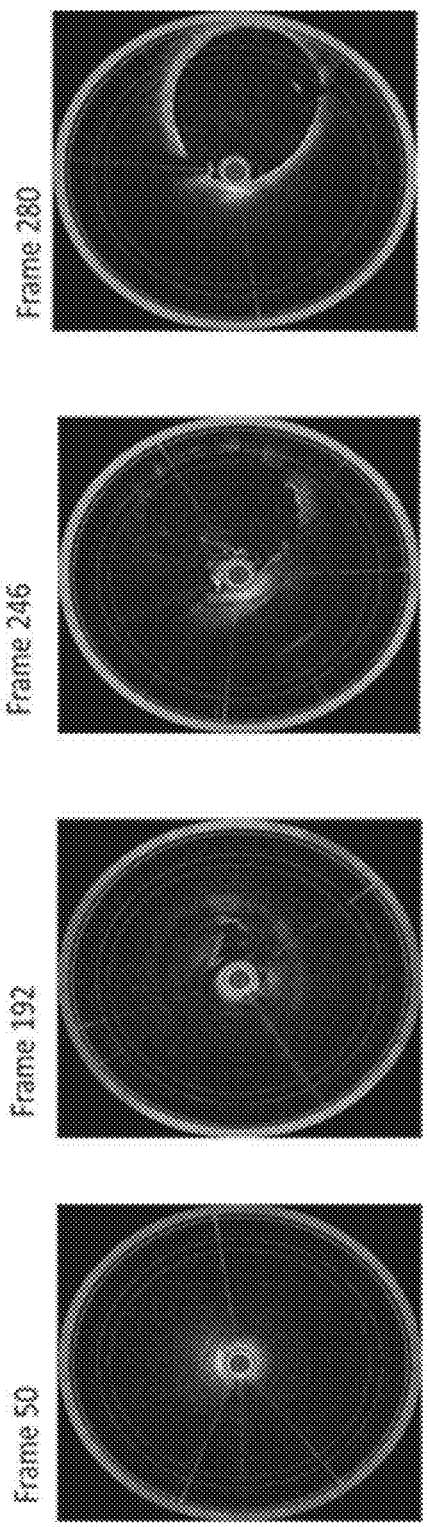

Here is the one example of the in-vivo animal study to flush with contrast media. The OCT and fluorescence or auto-fluorescence images were acquired before and after flushing. The averaged fluorescence or auto-fluorescence intensity was calculated as shown in FIG. 8B, and the OCT and fluorescence or auto-fluorescence images are shown in FIG. 8C at frame 50, frame 192, frame 246, and frame 280, respectively. The vessels are completely filled with blood at frame 50, and from frame 192 to 246, the contrast media flush out the blood, and partially see the clearance (transition). Then, in the subject experiment, the blood was cleared completely at frame 280 (as best shown in FIG. 8C).

In FIG. 8B, when the averaged fluorescence or auto-fluorescence intensity crosses the predetermined threshold, the pullback and/or image recording trigger is generated. Preferably, the trigger is generated in a case where the averaged intensity equals or crosses the predetermined threshold and the predetermined threshold is defined such that the system (e.g., the system 100, the system 100', the system 100", any other system discussed herein, etc.) is able to initiate pullback and/or imaging automatically, for example, once flushing is detected. As aforementioned, the trigger may be set to occur when the averaged intensity equals and/or crosses the predetermined threshold in one or more embodiments. In one or more embodiments, in a case where the threshold crossing and/or equaling condition is met, a notification may be sent to a user to initiate pullback and/or imaging manually as desired.

While imaging of coronary arteries is described by intravascular OCT and fluorescence system(s) in one or more of the aforementioned embodiments, imaging is not limited to only coronary arteries. In general, the methods, apparatuses, systems, and storage mediums discussed herein operate to generate a trigger signal based on a detected fluorescence or auto-fluorescence signal change or changes to control apparatuses, devices and/or systems to perform pullback and/or imaging (e.g., automatic or manual recording), for example, once a clear view is available (e.g., once blood or another preset, predetermined or target substance is flushed or cleared from the imaging path(s) as aforementioned). In one or more method embodiments of the present disclosure, high computational power is not necessary (e.g., relatively higher processing power is not needed compared to a situation where one or more features of the present disclosure are employed), and high-speed acquisition (e.g., relatively higher speed is achieved compared to a situation where one or more features of the present disclosure are not employed) is achieved.

One or more additional embodiments of the present disclosure may be employed to perform pullback and/or imaging (e.g., for imaging of coronary arteries by intravascular OCT system(s) and/or apparatus(es) discussed herein). The apparatuses, systems, methods and/or storage mediums for performing the one or more additional embodiments may be equivalent to the apparatuses, systems, methods and/or storage mediums for performing the aforementioned embodiments. For example, the subject one or more embodiments are capable of generating, or operate to generate, a trigger by using the fluorescence or auto-fluorescence intensities.

At least one difference or exception that the subject one or more embodiments includes involves how the fluorescence or auto-fluorescence intensities are processed. For example, in the one or more additional embodiments, the fluorescence or auto-fluorescence intensities may be processed to perform or calculate a second order derivation of the averaged signals (devAF) to monitor the signal differences over time. One or more embodiments may perform or calculate the second order derivation using the following equation (2):

$$devAF = \frac{\partial^2}{\partial t^2} aveAF, \qquad (2)$$

where devAF is the second order derivation of the averaged signals, and aveAF is the averaged signals (e.g., as defined above for equation (1), as otherwise averaged, etc.).

Once the change of the derivation (or derivative) is detected, the computer or processor (e.g., the computer or processor 1200, the computer or processor 1200', any other computer or processor discussed herein, etc.) operates to generate a trigger signal to initiate pullback and/or record images, automatically. In one or more embodiments, in a case where the derivation (or derivative) change is detected, a notification may be sent to a user to initiate pullback and/or imaging manually as desired.

Figure 9A:
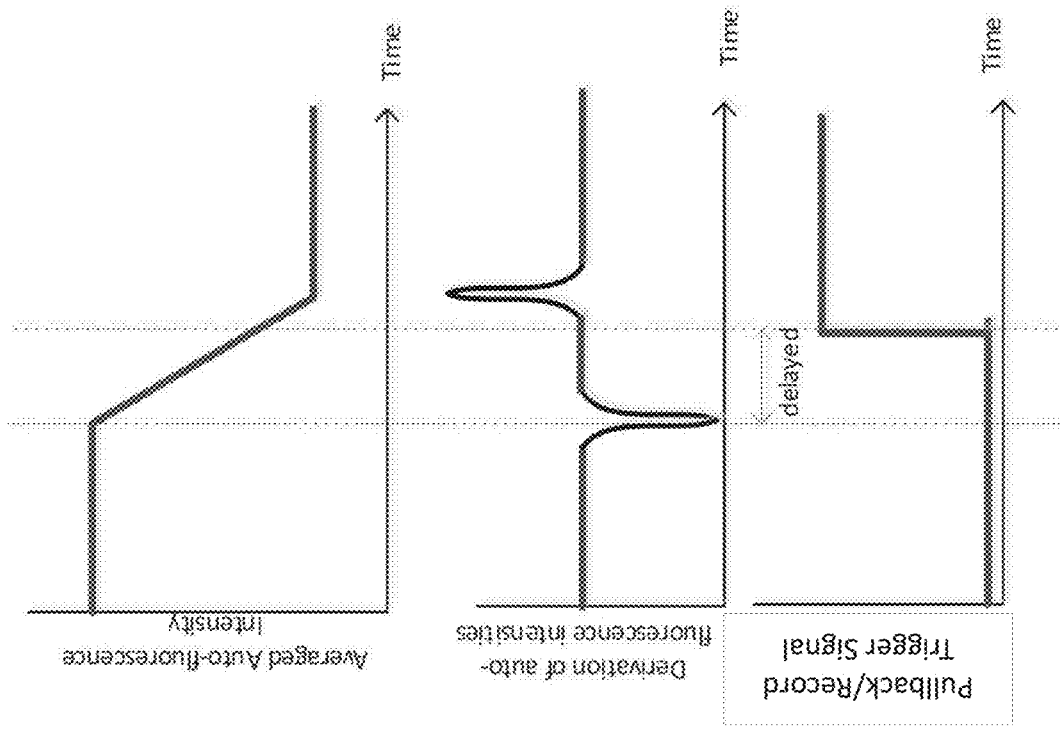
FIGS. 9A-9B are graphs showing time sequencings, respectively, to generate a trigger signal for recording one or more images in accordance with one or more aspects of the present disclosure.
Figure 9B:
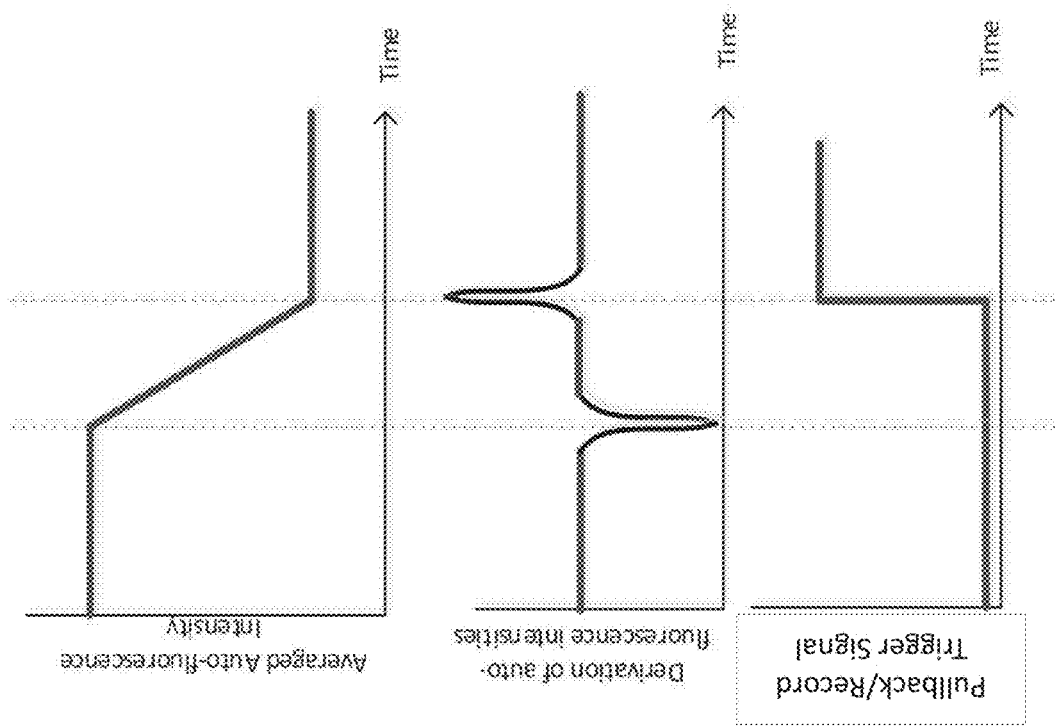

When the signals cross the positive and/or negative, the computer or processor (e.g., the computer or processor 1200, the computer or processor 1200', any other computer or processor discussed herein, etc.) operates to generate a trigger signal to start pullback and/or record images, automatically (or may prompt a user to provide authorization to perform same, may prompt a user to manually select one or both of such features, etc.). The time sequence is shown in FIGS. 9A and 9B. The predetermined delay feature described above also may be implemented to have proper time to flush blood (and/or any target or other target substance) completely, or sufficiently to achieve clear images. In FIGS. 9A and 9B, for example, the averaged fluorescence or auto-fluorescence intensity starts to decrease in a case where the derivation of the fluorescence or auto-fluorescence intensities changes first (e.g., changes negatively). In FIG. 9A, the pullback/recording trigger signal is generated in a case where the derivation of the fluorescence or auto-fluorescence intensities changes a second time (e.g., changes positively as shown in FIG. 9A, for example, where the averaged intensity levels out as the slope of the graph becomes less negative or becomes more positive). In one or more embodiments, a delay may be employed as aforementioned, as shown in FIG. 9B. The predetermined delay may be used after a first derivation change (best shown in FIG. 9B) and/or before a second derivation change. When the detected fluorescence or auto-fluorescence intensities are noisy during transition to blood clearance, the trigger generation with predetermined delay after detection of transition may work better in one or more embodiments. By way of at least one example, the trigger generation may become more robust to the noise.

One or more further embodiments of the present disclosure may be employed to perform pullback and/or imaging (e.g., for imaging of coronary arteries by intravascular OCT system(s) and/or apparatus(es) discussed herein). The apparatuses, systems, methods and/or storage mediums for performing the one or more further embodiments may be equivalent to the apparatuses, systems, methods and/or storage mediums for performing the aforementioned embodiments. For example, the subject one or more embodiments are capable of generating, or operate to generate, a trigger by using the fluorescence or auto-fluorescence intensities.

Figure 10:
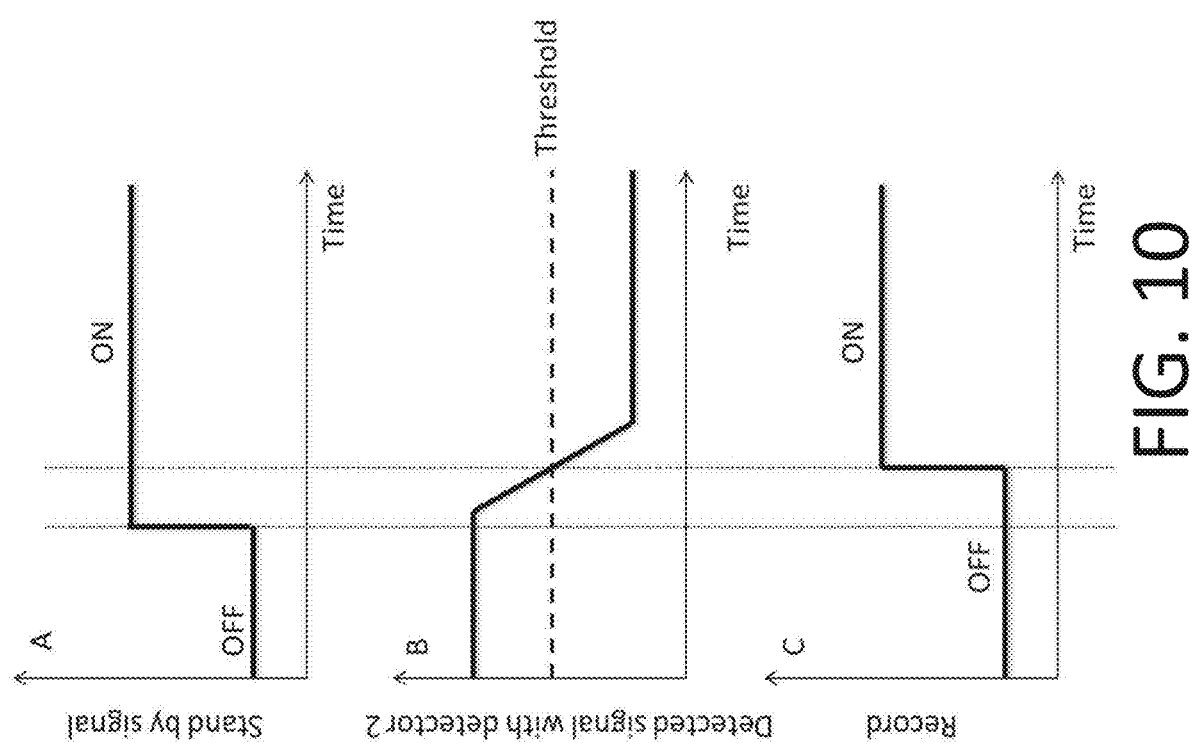
FIG. 10 is a graph showing a time sequence to generate a trigger signal for recording one or more images in accordance with one or more aspects of the present disclosure.

Additionally or alternatively, at least one difference or exception that the subject one or more further embodiments includes involves how the fluorescence or auto-fluorescence intensities are processed. For example, in the one or more additional embodiments, the trigger may be generated (see bottom portion of FIG. 10 showing an example where recording is turned on—in one or more embodiments the trigger may control other features, such as, but not limited to, pullback and/or recording as aforementioned) in a case where another "stand-by signal" (or "ready mode") is on or active (see top portion of FIG. 10) and a detected signal (e.g., with a detector 2, such as the fluorescence or auto-fluorescence detector(s) 107 discussed above, the DAQ 2 128, etc.) crosses the predetermined or preset threshold (see middle portion of FIG. 10). In one or more embodiments, devices or apparatuses, such as, but not limited to, a light source(s), a shutter(s), a computer or processor(s), and/or a motor(s) (e.g., see discussions herein of various embodiments of the subject devices or apparatuses), may start by receiving the trigger.

In one or more alternative embodiments, a free space beam combiner, which is located inside an FORJ, may be provided as shown in FIG. 7. The embodiment of FIG. 7 is the same as the embodiment shown in FIG. 4, with the following exceptions: the stator 306b' of the rotary junction 306' in FIG. 7 includes two optical fibers (and not three) because the multi-mode fiber 508 and the GRIN lens 501d are removed, and the stator 306b' of the rotary junction 306' includes a double clad fiber 506 being used with GRIN lens 501a (instead of the single mode fiber 507a as shown in FIG. 4). OCT light goes through the core of the double clad fiber 506 in the stator 306', and is then collimated with the GRIN lens 50a. The collimated light is coupled into the core of the double clad fiber 506 in the rotor 306a'. Excitation light, with wavelength shorter than that of OCT light, is converged and focused with the GRIN lens 501c at the middle (or at a predetermined position) of the optical path to GRIN lens 501b. Then, the light is coupled into mostly the core of the double clad fiber 506 in the rotor 306a' of the rotary junction 306'. Fluorescence light from the sample (e.g., the sample 106) is delivered through mostly the clad of the double clad fiber 506 in rotor 306a'. Then, the light is coupled into the clad of the double clad fiber 506 in the stator 306b'. To separate OCT light and fluorescence light, a double clad fiber coupler may be used either inside the PIU 110 or in the imaging subsystem. Dichroic filter 502 of FIG. 7 is used to separate excitation light and the rest of fluorescence and OCT lights. The double clad fiber 506 of the stator 306b' is connected to a core/clad beam splitter to separate OCT and fluorescence light. As such, a simple and compact FORJ may be achieved with this configuration because of a lack of the free-space optical fluorescence channel. Also, it is easier to fabricate the beam combiner because OCT and fluorescence lights are coupled using a common double clad fiber (e.g., the fiber 506). The FORJ 306' may be used in place of the FORJ 306 as discussed above as shown schematically in FIG. 2B. In one or more embodiments, a mirror, a ferrule, a sleeve and/or epoxy as discussed in the present disclosure may be optional, and the fibers, lenses and a dichroic filter may be used without one or more of the mirror, the ferrule, the sleeve and/or the epoxy.

Descriptions of like-numbered elements present in the system 100, the system 100', the system 100" and/or the rotary junction 306' and already described above, such as, but not limited to, for the system 100', the system 100", and/or the rotary junction 306, shall not be repeated, and are incorporated by reference herein in their entireties.

In at least one embodiment, the console 1200, 1200' operates to control motions of the motor and translation motorized stage (hereinafter referred to as "motor" or "motor and stage") 139, acquires intensity data from the at least one detector(s) 107, and displays the scanned image (e.g., on a monitor or screen such as a display, screen or monitor 1209 as shown in the console 1200 of FIG. 11 and/or the console 1200' of FIG. 12 as further discussed below). In one or more embodiments, the console 1200, 1200' operates to change a speed of the motor 139 and/or to stop the motor 139. The motor 139 may be a stepping or a DC servo motor to control the speed and increase position accuracy.

In one or more embodiments, the console or computer 1200, 1200' operates to control motions of the rotary junction 306, the rotary junction 306', the motor 139, the catheter 120 and/or one or more other above-described components of the system 100, the system 100', and/or the system 100" (or any other systems discussed herein or that may use one or more features of the present disclosure). In at least one embodiment, the console or computer 1200, 1200' operates to acquire intensity data from the at least one detector 107 of the OCT sub-system and the fluorescence sub-system, and displays the image(s) (e.g., on a monitor or screen such as a display, screen or monitor 1209 as shown in the console 1200 of FIG. 11 and/or the console 1200' of FIG. 12 as further discussed below). The output of the one or more components of the system 100, the system 100', and/or the system 100" is acquired with the at least one detector 107 of the OCT sub-system and with the at least one detector 107 of the fluorescence sub-system, e.g., such as, but not limited to, photodiodes, Photomultiplier tube(s) (PMTs), line scan camera(s), or multi-array camera(s). Electrical analog signals obtained from the output of the system 100, the system 100' and/or the system 100" or one or more components thereof are converted to digital signals to be analyzed with a computer, such as, but not limited to, the computer 1200, 1200' (e.g., as shown in FIGS. 1-2B and 11-12). In one or more embodiments, the light source 101 may be a radiation source or a broadband light source that radiates in a broad band of wavelengths. In one or more embodiments, a Fourier analyzer including software and electronics may be used to convert the electrical analog signals into an optical spectrum. In some embodiments, the at least one detector 107 comprises three detectors configured to detect three different bands of light. In one or embodiments where the at least one detector 107 is a plurality of detectors 107, each of the detectors 107 may be made of three detectors configured to detect three different bands of light.

A computer, such as the console or computer 1200, 1200', may perform any of the aforementioned method step(s), for any apparatus, system, trigger, and/or FORJ, including, but not limited to, system 100, system 100', system 100", FORJ 306, FORJ 306', any trigger discussed herein, etc.

In one or more embodiments, a SEE probe and/or system may use a FORJ (e.g., the FORJ 306, the FORJ 306', etc.) with a connection member or interface module. For example, the connection member or interface module may include a rotary junction for either a SEE probe. In such a SEE system, the rotary junction may be at least one of: a contact rotary junction, a lenseless rotary junction, a lens-based rotary junction, a rotary junction as described herein, etc. The rotary junction may be a one channel rotary junction or a two channel rotary junction. By way of at least one example, in a SEE device one or more light sources may be used, and the light may be split into at least two (2) wavelength ranges for use with one or more embodiments of a FORJ of the present disclosure.

Unless otherwise discussed herein, like numerals indicate like elements. For example, while variations or differences exist between FORJs and/or the systems, such as, but not limited to, the FORJ 306, the FORJ 306', the system 100, the system 100', the system 100", etc., one or more features thereof may be the same or similar to each other, such as, but not limited to, the light source 101 or other component(s) thereof (e.g., the console 1200, the console 1200', etc.). Those skilled in the art will appreciate that the light source 101, the at least one detector 107 and/or one or more other elements of the system 100, may operate in the same or similar fashion to those like-numbered elements of one or more other systems, such as, but not limited to, the system 100', the system 100", etc. as discussed herein. Those skilled in the art will appreciate that alternative embodiments of the system 100, the system 100', the system 100", the FORJ 306, the FORJ 306' and/or one or more like-numbered elements of one of such systems or FORJs, any trigger(s) discussed herein, while having other variations as discussed herein, may operate in the same or similar fashion to the like-numbered elements of any of the other systems (or component(s) thereof) or FORJs (or component(s) thereof) or other trigger(s) discussed herein. Indeed, while certain differences exist between the system 100 and the system 100' or the system 100", and between FORJ 306 and FORJ 306', as discussed herein, there are similarities. Likewise, while the console or computer 1200 may be used in one or more systems (e.g., the system 100, the system 100', the system 100", a system for manufacturing an FORJ (e.g., the FORJ 306, the FORJ 306', etc.), etc.), to control an FORJ (e.g., the FORJ 306, the FORJ 306', etc.) and/or to control or employ one or more triggers, one or more other consoles or computers, such as the console or computer 1200', may be used additionally or alternatively.

There are many ways to compute rotation, intensity, or any other measurement discussed herein, to control and/or manufacture an FORJ, and/or to employ one or more triggers (e.g., a fluorescence trigger or triggers, an auto-fluorescence trigger or triggers, a NIRAF trigger or triggers, etc.), digital as well as analog. In at least one embodiment, a computer, such as the console or computer 1200, 1200', may be dedicated to control and monitor a FORJ, one or more triggers (e.g., a fluorescence trigger or triggers, an auto-fluorescence trigger or triggers, a NIRAF trigger or triggers, etc.) and devices, systems, methods and/or storage mediums for use therewith described herein.

The electric signals used for imaging may be sent to one or more processors, such as, but not limited to, a computer 1200 (see e.g., FIGS. 1-2B and 11), a computer 1200' (see e.g., FIG. 12), any other processor discussed herein, etc. as discussed further below, via cable(s) or wire(s), such as, but not limited to, the cable(s) or wire(s) 118 (see FIG. 11).

Various components of a computer system 1200 (see e.g., the console or computer 1200 as shown in FIGS. 1-2B) are provided in FIG. 11. A computer system 1200 may include a central processing unit ("CPU") 1201, a ROM 1202, a RAM 1203, a communication interface 1205, a hard disk (and/or other storage device) 1204, a screen (or monitor interface) 1209, a keyboard (or input interface; may also include a mouse or other input device in addition to the keyboard) 1210 and a BUS or other connection lines (e.g., connection line 1213) between one or more of the aforementioned components (e.g., as shown in FIG. 11). In addition, the computer system 1200 may comprise one or more of the aforementioned components. For example, a computer system 1200 may include a CPU 1201, a RAM 1203, an input/output (I/O) interface (such as the communication interface 1205) and a bus (which may include one or more lines 1213 as a communication system between components of the computer system 1200; in one or more embodiments, the computer system 1200 and at least the CPU 1201 thereof may communicate with the one or more aforementioned components of a FORJ or a device or system using same, such as, but not limited to, the system 100, the system 100', and/or the system 100", discussed herein above, via one or more lines 1213), and one or more other computer systems 1200 may include one or more combinations of the other aforementioned components. The CPU 1201 is configured to read and perform computer-executable instructions stored in a storage medium. The computer-executable instructions may include those for the performance of the methods and/or calculations described herein. The computer system 1200 may include one or more additional processors in addition to CPU 1201, and such processors, including the CPU 1201, may be used for controlling and/or manufacturing a FORJ, for employing a trigger(s) (e.g., a fluorescence trigger or triggers, an auto-fluorescence trigger or triggers, a NIRAF trigger(s), a trigger for pullback and/or image recording, etc.), and/or a device, system or storage medium for use with same. The system 1200 may further include one or more processors connected via a network connection (e.g., via network 1206). The CPU 1201 and any additional processor being used by the system 1200 may be located in the same telecom network or in different telecom networks (e.g., performing FORJ manufacturing and/or use technique(s) may be controlled remotely, performing one or more method(s) discussed herein remotely, using a trigger(s) remotely, etc.).

The I/O or communication interface 1205 provides communication interfaces to input and output devices, which may include the light source 101, a FORJ (e.g., the FORJ 306, the FORJ 306', etc.), a microphone, a communication cable and a network (either wired or wireless), a keyboard 1210, a mouse (see e.g., the mouse 1211 as shown in FIG. 12), a touch screen or screen 1209, a light pen and so on. The Monitor interface or screen 1209 provides communication interfaces thereto.

Any methods and/or data of the present disclosure, such as the methods for using and/or manufacturing a FORJ, the methods for using or employing one or more triggers (e.g., a fluorescence trigger or triggers, an auto-fluorescence trigger or triggers, a NIRAF trigger or triggers, etc.), etc., and/or a device, system or storage medium for use with same, as discussed herein, may be stored on a computer-readable storage medium. A computer-readable and/or writable storage medium used commonly, such as, but not limited to, one or more of a hard disk (e.g., the hard disk 1204, a magnetic disk, etc.), a flash memory, a CD, an optical disc (e.g., a compact disc ("CD") a digital versatile disc ("DVD"), a Blu-ray™ disc, etc.), a magneto-optical disk, a random-access memory ("RAM") (such as the RAM 1203), a DRAM, a read only memory ("ROM"), a storage of distributed computing systems, a memory card, or the like (e.g., other semiconductor memory, such as, but not limited to, a non-volatile memory card, a solid state drive (SSD) (see SSD 1207 in FIG. 12), SRAM, etc.), an optional combination thereof, a server/database, etc. may be used to cause a processor, such as, the processor or CPU 1201 of the aforementioned computer system 1200 to perform the steps of the methods disclosed herein. The computer-readable storage medium may be a non-transitory computer-readable medium, and/or the computer-readable medium may comprise all computer-readable media, with the sole exception being a transitory, propagating signal. The computer-readable storage medium may include media that store information for predetermined or limited or short period(s) of time and/or only in the presence of power, such as, but not limited to Random Access Memory (RAM), register memory, processor cache(s), etc. Embodiment(s) of the present disclosure may also be realized by a computer of a system or apparatus that reads out and executes computer executable instructions (e.g., one or more programs) recorded on a storage medium (which may also be referred to more fully as a "non-transitory computer-readable storage medium") to perform the functions of one or more of the above-described embodiment(s) and/or that includes one or more circuits (e.g., application specific integrated circuit (ASIC)) for performing the functions of one or more of the above-described embodiment(s), and by a method performed by the computer of the system or apparatus by, for example, reading out and executing the computer executable instructions from the storage medium to perform the functions of one or more of the above-described embodiment(s) and/or controlling the one or more circuits to perform the functions of one or more of the above-described embodiment(s).

In accordance with at least one aspect of the present disclosure, the methods, systems, and computer-readable storage mediums related to the processors, such as, but not limited to, the processor of the aforementioned computer 1200, the processor of computer 1200', etc., as described above may be achieved utilizing suitable hardware, such as that illustrated in the figures. Functionality of one or more aspects of the present disclosure may be achieved utilizing suitable hardware, such as that illustrated in FIG. 11. Such hardware may be implemented utilizing any of the known technologies, such as standard digital circuitry, any of the known processors that are operable to execute software and/or firmware programs, one or more programmable digital devices or systems, such as programmable read only memories (PROMs), programmable array logic devices (PALs), etc. The CPU 1201 (as shown in FIG. 11) may also include and/or be made of one or more microprocessors, nanoprocessors, one or more graphics processing units ("GPUs"; also called a visual processing unit ("VPU")), one or more Field Programmable Gate Arrays ("FPGAs"), or other types of processing components (e.g., application specific integrated circuit(s) (ASIC)). Still further, the various aspects of the present disclosure may be implemented by way of software and/or firmware program(s) that may be stored on suitable storage medium (e.g., computer-readable storage medium, hard drive, etc.) or media (such as floppy disk(s), memory chip(s), etc.) for transportability and/or distribution. The computer may include a network of separate computers or separate processors to read out and execute the computer executable instructions. The computer executable instructions may be provided to the computer, for example, from a network or the storage medium.

As aforementioned, hardware structure of an alternative embodiment of a computer or console 1200' is shown in FIG. 12. The computer 1200' includes a central processing unit (CPU) 1201, a graphical processing unit (GPU) 1215, a random access memory (RAM) 1203, a network interface device 1212, an operation interface 1214 such as a universal serial bus (USB) and a memory such as a hard disk drive or a solid state drive (SSD) 1207. Preferably, the computer or console 1200' includes a display 1209. The computer 1200' may connect with a rotary junction (e.g., the FORJ 306, the FORJ 306', etc.), the motor 139 and/or one or more other components of a system (e.g., the system 100, the system 100', the system 100'', etc.) via the operation interface 1214 or the network interface 1212. A computer, such as the computer 1200', may include the FORJ 306 or 306' and/or the motor 139 in one or more embodiments. The operation interface 1214 is connected with an operation unit such as a mouse device 1211, a keyboard 1210 or a touch panel device. The computer 1200' may include two or more of each component. Alternatively, the CPU 1201 or the GPU 1215 may be replaced by the field-programmable gate array (FPGA), the application-specific integrated circuit (ASIC) or other processing unit depending on the design of a computer, such as the computer 1200, the computer 1200', etc.

A computer program is stored in the SSD 1207, and the CPU 1201 loads the program onto the RAM 1203, and executes the instructions in the program to perform one or more processes described herein, as well as the basic input, output, calculation, memory writing and memory reading processes.

The computer, such as the computer 1200, 1200', communicates with the PUI 110, the rotary junction (e.g., the rotary junction 306, the rotary junction 306', etc.), the motor 139, the catheter 120 and/or one or more other components of a system, such as the system 100, 100', 100", etc., to perform imaging (e.g., with pullback and/or image recording using a trigger or triggers), and reconstructs an image from the acquired intensity data. The monitor or display 1209 displays the reconstructed image, and may display other information about the imaging condition or about an object to be imaged. The monitor 1209 also provides a graphical user interface for a user to operate a system (e.g., the system 100, the system 100', the system 100", etc.), for example when performing OCT or other imaging technique. An operation signal is input from the operation unit (e.g., such as, but not limited to, a mouse device 1211, a keyboard 1210, a touch panel device, etc.) into the operation interface 1214 in the computer 1200', and corresponding to the operation signal the computer 1200' instructs the system (e.g., the system 100, the system 100', the system 100", etc.) to set or change the imaging condition, and to start or end the imaging. The laser source 101 of an OCT sub-system and/or the laser source 101 of a fluorescence sub-system as aforementioned may have interfaces to communicate with the computers 1200, 1200' to send and receive the status information and the control signals.

The present disclosure and/or one or more components of devices, systems and storage mediums, and/or methods, thereof also may be used in conjunction with any suitable optical assembly including, but not limited to, SEE probe technology, such as in U.S. Pat. Nos. 6,341,036; 7,447,408; 7,551,293; 7,796,270; 7,859,679; 8,045,177; 8,145,018; 8,838,213; 9,254,089; 9,295,391; 9,415,550; 9,557,154 and Patent Application Publication Nos. US2017/0035281; WO2015/116951; WO2015/116939; WO2017/024145; and US2018/0017778, each of which patents, patent publications and patent application(s) are incorporated by reference herein in their entireties.

Similarly, the present disclosure and/or one or more components of devices, systems and storage mediums, and/or methods, thereof also may be used in conjunction with optical coherence tomography probes. Such probes include, but are not limited to, the OCT imaging systems disclosed in U.S. Pat. Nos. 7,872,759; 8,289,522; and 8,928,889 to Tearney et al. and arrangements and methods of facilitating photoluminescence imaging, such as those disclosed in U.S. Pat. No. 7,889,348 to Tearney et al., as well as the disclosures directed to multimodality imaging disclosed in U.S. Pat. No. 9,332,942 and U.S. Patent Publication Nos. 2010/0092389, 2012/0101374 and 2016/0228097, each of which patents, patent publications and patent application(s) are incorporated by reference herein in their entireties.

Also similarly, the present disclosure and/or one or more components of devices, systems and storage mediums, and/or methods, thereof also may be used in conjunction with rotary joints and/or methods of making and/or using rotary joints. Such rotary joints and methods of making and/or using rotary joints include, but are not limited to, the rotary joints and methods as disclosed in U.S. Pat. Pub. No. 2018/0348439, published Dec. 6, 2018, which is incorporated by reference herein in its entirety.

Although the disclosure herein has been described with reference to particular embodiments, it is to be understood that these embodiments are merely illustrative of the principles and applications of the present disclosure (and are not limited thereto). It is therefore to be understood that numerous modifications may be made to the illustrative embodiments and that other arrangements may be devised without departing from the spirit and scope of the present disclosure.

The scope of the following claims is to be accorded the broadest interpretation so as to encompass all such modifications and equivalent structures and functions.

The invention claimed is:

1. An imaging apparatus or system comprising:
an interference optical system that operates to: (i) receive and divide light from a light source into a first light with which an object or sample is to be irradiated and which travels along a sample arm of the interference optical system and a second reference light, (ii) send the second reference light along a reference arm of the interference optical system for reflection off of a reference reflection of the interference optical system, and (iii) generate interference light by causing reflected or scattered light of the first light with which the object or sample has been irradiated and the reflected second reference light to combine or recombine, and to interfere, with each other, the interference light generating one or more interference patterns; and
at least one detector that operates to acquire at least one type of one or more signals,
wherein the imaging apparatus or system generates and/or uses a trigger signal that operates to monitor one or more changes in the one or more signals obtained by the at least one detector to control the imaging apparatus or system, and the one or more signals obtained by the at least one detector are one or more fluorescence or auto-fluorescence intensity signals.

2. The imaging apparatus or system of claim 1, wherein the imaging apparatus or system operates to one or more of:
(i) perform a pullback and/or record image(s) in response to generation of the trigger signal or in response to a change in a state of the trigger signal based on a change in the one or more signals obtained by the at least one detector; and/or
(ii) use or generate the trigger signal to perform the pullback and/or the recordation of the image(s) using less computational power and achieving higher acquisition speed compared to a situation where the trigger signal is not used or generated.

3. The imaging apparatus or system of claim 1, wherein one or more of:
(i) the interference optical system includes at least two clads or claddings; and/or
(ii) the interference optical system includes a double clad fiber.

4. The imaging apparatus or system of claim 1, wherein one or more of:
(i) the first light has a wavelength that is shorter than a wavelength of the second light;
(ii) the second light is delivered as a collimated beam at or to the beam combiner;
and/or
(iii) the first light is delivered after focusing in a middle of an optical path from a stator to a rotor of a rotary joint or junction.

5. The imaging apparatus or system of claim 1, further comprising one or more of the following: a processor or computer that operates to generate or use the trigger signal, a pullback translational stage, a shutter, and a light source.

6. The imaging apparatus or system of claim 1, wherein one or more of the following:
(i) the at least one detector further operates to continuously acquire the interference light and/or the one or more interference patterns to measure the interference or the one or more interference patterns between the combined or recombined light;

(ii) the interference optical system is an Optical Coherence Tomography (OCT) system;
(iii) the imaging apparatus or system is a multi-modality imaging apparatus or system; and/or
(iv) the imaging apparatus or system is a multi-modality imaging apparatus or system, where the multi-modalities comprise OCT and fluorescence or auto-fluorescence.

7. The imaging apparatus or system of claim 6, further comprising a processor that operates to:
process the detected one or more fluorescence or auto-fluorescence intensity signals to average multiple A-lines of a frame; and
generate or use the trigger signal to control the imaging apparatus or system to perform the pullback and/or to record the image(s) in a case where fluorescence or auto-fluorescence intensities of the one or more fluorescence or auto-fluorescence intensity signals cross or equal a predetermined threshold.

8. The imaging apparatus or system of claim 7, wherein the processor further operates to one or more of the following:
(i) use a predetermined delay before the imaging apparatus or system performs the pullback and/or the recordation of the image(s);
(ii) flushing blood, blood cells, or any other target substance during the predetermined delay and before performing the pullback and/or the recordation of the image(s);
(iii) flushing blood, blood cells, or any other target substance to lower or change the fluorescence or auto-fluorescence intensities to equal or cross over the predetermined threshold;
(iv) in response to a detection that the flushing or clearance has been completed, initiate the pullback and/or the recordation of the image(s) automatically or prompt a user of the imaging device or system to manually initiate the pullback and/or the recordation of the image(s);
(v) generate or use the trigger signal to control the imaging apparatus or system to perform the pullback and/or to record the image(s) in a case where a stand-by signal or a ready mode is on and where the averaged fluorescence or auto-fluorescence intensities of the one or more fluorescence or auto-fluorescence intensity signals cross or equal the predetermined threshold; and/or
(vi) control clearing or flushing of an artery in an intravascular or coronary artery application using a contrast agent, saline, dextran or other liquid(s).

9. The imaging apparatus or system of claim 6, further comprising a processor that operates to:
process the detected one or more fluorescence or auto-fluorescence intensity signals to calculate a second order derivation or derivative of averaged fluorescence or auto-fluorescence intensity signals;
monitor the calculated second order derivation or derivative over time to detect a change of the calculated second order derivation or derivative; and
generate or use the trigger signal to control the imaging apparatus or system to perform the pullback and/or to record the image(s) in a case where the calculated second order derivation or derivative crosses or becomes a positive value or a negative value.

10. The imaging apparatus or system of claim 9, wherein the processor further operates to one or more of the following:
(i) use a predetermined delay before the imaging apparatus or system performs the pullback and/or the recordation of the image(s);
(ii) flushing blood, blood cells, or any other target substance during the predetermined delay and before performing the pullback and/or the recordation of the image(s);
(iii) flushing blood, blood cells, or any other target substance to lower or change the fluorescence or auto-fluorescence intensities to equal or cross over the predetermined threshold;
(iv) in response to a detection that the flushing or clearance has been completed, initiate the pullback and/or the recordation of the image(s) automatically or prompt a user of the imaging device or system to manually initiate the pullback and/or the recordation of the image(s);
(v) generate or use the trigger signal to control the imaging apparatus or system to perform the pullback and/or to record the image(s) in a case where a stand-by signal or a ready mode is on and where the averaged fluorescence or auto-fluorescence intensities of the one or more fluorescence or auto-fluorescence intensity signals cross or equal the predetermined threshold; and/or
(vi) control clearing or flushing of an artery in an intravascular or coronary artery application using a contrast agent, saline, dextran or other liquid(s).

11. The imaging apparatus or system of claim 1, further comprising:
a fiber optic rotary joint (FORJ) comprising:
a beam combiner;
a rotor that operates to rotate and that includes a common optical fiber connected to or part of the beam combiner; and
a stator that operates to be stationary in the fiber optic rotary joint and that includes at least two optical fibers, a first of the at least two optical fibers operating to guide at least the first light and being connected to or part of the beam combiner and a second of the at least two optical fibers operating to guide a third light and being connected to or part of the beam combiner,
wherein the beam combiner operates to combine the first and third lights from the at least two optical fibers such that the combined light couples, or substantially couples, into a core of the common optical fiber.

12. The imaging apparatus or system of claim 11, wherein the combined light operates to irradiate the sample, and the FORJ includes at least one dichroic filter to separate the combined light into OCT light to be transmitted to a first detector of the at least one detector and into fluorescent or autofluorescent light to be transmitted to a second detector of the at least one detector.

13. The imaging apparatus or system of claim 11, further comprising one or more of:
(i) at least two light sources, a first of the at least two light sources operating to produce the first light, which is an OCT light, and a second of the at least two light sources operating to produce the third light, which is an excitation light; and/or
(ii) at least one of a motor and a processor that operates to rotate the rotor of the FORJ.

14. The imaging apparatus or system of claim 1, further comprising:

a Multi-modality fiber optic rotary joint (FORJ) comprising:
  a rotor and a static beam combiner;
  a first optical fiber and a first lens in the rotor;
  a second lens and a second optical fiber in the beam combiner; and
  a third lens and a third optical fiber in the beam combiner;
  wherein:
  (i) the first lens and the second lens are configured such that the first light couples to and from a core of the first optical fiber to a core of the second optical fiber, and
  (ii) the first lens and the third lens are configured such that a third light from a core of the third optical fiber is coupled to the core of the first optical fiber with an intermediate focus in between the first lens and the third lens.

* * * * *